(12) United States Patent
Luo et al.

(10) Patent No.: US 12,229,224 B2
(45) Date of Patent: Feb. 18, 2025

(54) MEDICAL IMAGE PROCESSING METHOD AND APPARATUS, AND MEDICAL IMAGE RECOGNITION METHOD AND APPARATUS

(71) Applicant: TENCENT TECHNOLOGY (SHENZHEN) COMPANY LIMITED, Shenzhen (CN)

(72) Inventors: Lishu Luo, Shenzhen (CN); Hong Shang, Shenzhen (CN); Zhongqian Sun, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 774 days.

(21) Appl. No.: 17/469,850

(22) Filed: Sep. 8, 2021

(65) Prior Publication Data

US 2021/0406591 A1 Dec. 30, 2021

Related U.S. Application Data

(63) Continuation of application No. PCT/CN2020/103921, filed on Jul. 24, 2020.

(30) Foreign Application Priority Data

Aug. 29, 2019 (CN) .......................... 201910809281.8

(51) Int. Cl.
*G06F 18/2431* (2023.01)
*A61B 1/00* (2006.01)
(Continued)

(52) U.S. Cl.
CPC .......... *G06F 18/2431* (2023.01); *A61B 5/015* (2013.01); *A61B 5/4887* (2013.01);
(Continued)

(58) Field of Classification Search
None
See application file for complete search history.

(56) References Cited

U.S. PATENT DOCUMENTS 10,600,334 B1 * 3/2020 Zhang ................. A61B 5/1128
10,620,713 B1 * 4/2020 Ng ............................ G06T 7/73
(Continued)

FOREIGN PATENT DOCUMENTS

CA 2969038 C * 7/2023 .......... G06K 9/0014
CN 107077736 A 8/2017
(Continued)

OTHER PUBLICATIONS

The State Intellectual Property Office of the People's Republic of China (SIPO) Office Action 1 for for 201910810299.X Aug. 27, 2020 18 Pages (including translation).
(Continued)

*Primary Examiner* — Mohammed Rachedine
(74) *Attorney, Agent, or Firm* — Anova Law Group, PLLC

(57) ABSTRACT

A medical image processing method is provided to a data processing device. The method includes obtaining a medical image, obtaining a feature map and a medical image content recognition result that correspond to the medical image by using a medical image classification model, or obtaining the feature map and a lesion classification result that correspond to the medical image by using the medical classification model, the feature map including N channels, N being an integer greater than 1, generating a thermodynamic diagram corresponding to the medical image content recognition result or the lesion classification result according to the feature map and a weight parameter set, the weight parameter set including N weight parameters, the weight parameters having a correspondence with the channels, and generating an image recognition result corresponding to the medical image according to the thermodynamic diagram.

19 Claims, 18 Drawing Sheets

(51) Int. Cl.
  *A61B 5/00* (2006.01)
  *A61B 5/01* (2006.01)
  *G06F 18/24* (2023.01)
  *G06N 3/045* (2023.01)
  *G06N 3/08* (2023.01)
  *G06T 7/00* (2017.01)
  *G06T 11/00* (2006.01)
  *G06V 10/44* (2022.01)
  *G06V 10/764* (2022.01)
  *G06V 10/82* (2022.01)
  *G16H 30/20* (2018.01)
  *G16H 50/20* (2018.01)

(52) U.S. Cl.
  CPC .......... *A61B 5/7267* (2013.01); *G06T 7/0012* (2013.01); *G06T 11/00* (2013.01); *G06V 10/44* (2022.01); *G06T 2207/20084* (2013.01); *G06T 2207/30096* (2013.01); *G06V 2201/03* (2022.01)

(56) References Cited

U.S. PATENT DOCUMENTS

| | | |
|---|---|---|
| 2016/0063720 A1 | 3/2016 | Han et al. |
| 2018/0060652 A1 | 3/2018 | Zhang et al. |
| 2018/0075581 A1 | 3/2018 | Shi et al. |

FOREIGN PATENT DOCUMENTS

| | | | | | |
|---|---|---|---|---|---|
| CN | 109544510 A | | 3/2019 | | |
| CN | 109858482 A | * | 6/2019 | | |
| CN | 110009052 A | | 7/2019 | | |
| CN | 110009679 A | | 7/2019 | | |
| CN | 110084794 A | | 8/2019 | | |
| CN | 110136103 A | * | 8/2019 | .......... | G06F 18/241 |
| CN | 110504029 A | | 11/2019 | | |
| CN | 110188766 B | * | 6/2023 | .......... | G06K 9/4671 |

OTHER PUBLICATIONS

The World Intellectual Property Organization (WIPO) International Search Report for PCT/CN2020/103921 Oct. 28, 2020 7 Pages (including translation).

Karen Simonyan et al., "Deep Inside Convolutional Networks: Visualising Image Classification Models and Saliency Maps," In Proc. ICLR, 2014. 8 pages.

Matthew D. Zeiler et al., "Visualizing and Understanding Convolutional Networks," In European conference on computer vision, pp. 818-833, Springer, 2014. 16 pages.

Bolei Zhou et al., "Learning Deep Features for Discriminative Localization," CVPR 2016, pp. 2921-2929. 9 pages.

Ramprasaath R. Selvaraju et al., "Grad-CAM: Visual Explanations from Deep Networks via Gradient-Based Localization," ICCV. 2017, pp. 618-626. 9 pages.

* cited by examiner (a)     (b)

(a)     (b)

(a)     (b)     (c)

US 12,229,224 B2

MEDICAL IMAGE PROCESSING METHOD AND APPARATUS, AND MEDICAL IMAGE RECOGNITION METHOD AND APPARATUS

RELATED APPLICATION(S)

This application is a continuation application of PCT Patent Application No. PCT/CN2020/103921, filed on Jul. 24, 2020, which claims priority to Chinese Patent Application No. 201910809281.8, entitled "MEDICAL IMAGE PROCESSING METHOD AND APPARATUS, AND MEDICAL IMAGE RECOGNITION METHOD AND APPARATUS" filed with the China National Intellectual Property Administration on Aug. 29, 2019, all of which are incorporated herein by reference in entirety.

FIELD OF THE TECHNOLOGY

The present disclosure relates to the field of artificial intelligence (AI), and in particular, to medical image processing and medical image recognition.

BACKGROUND

With the development of computer science technologies, a deep learning (DL) method has been applicable to diagnosis of a medical image in many jobs, and therefore phenomena of missed diagnosis and misdiagnosis caused by inexperienced doctors or excessive fatigue of doctors can be alleviated to some extent.

In a DL-based medical image diagnosis method, data of a large quantity of images may need to be first collected, and the images are annotated by professional doctors; and a DL model is then trained by using the annotated images, to enable the trained DL model to fit a mapping relationship between an input image and a corresponding label. An unannotated original medical image is inputted to the model, to obtain a corresponding lesion class.

However, a DL-based model is often a black box model, which focuses on only an overall function, where an output result is only one vector representing a class, and a discriminative region on which the classification made by the model is based is in general unknown. Such a black box model often is deficient for medical diagnosis, and consequently reduces the reliability of diagnosis based on the medical image.

SUMMARY

Embodiments of the present disclosure provide a medical image processing method and apparatus, and a medical image recognition method and apparatus, which not only provide good interpretability for a model, but also provide a powerful basis for automatic diagnosis, so that the model is more convincing, thereby improving the reliability of diagnosis based on a medical image.

In one aspect, the present disclosure provides a medical image processing method, performed by a data processing device, the method including: obtaining a medical image; obtaining a feature map and a medical image content recognition result that correspond to the medical image by using a medical image classification model, or obtaining the feature map and a lesion classification result that correspond to the medical image by using the medical classification model, the feature map including N channels, N being an integer greater than 1; generating a thermodynamic diagram corresponding to the medical image content recognition result or the lesion classification result according to the feature map and a weight parameter set, the weight parameter set including N weight parameters, the weight parameters having a correspondence with the channels; and generating an image recognition result corresponding to the medical image according to the thermodynamic diagram.

In another aspect, the present disclosure provides a medical image processing apparatus, the medical image processing apparatus including: a memory storing computer program instructions; and a processor coupled to the memory and configured to execute the computer program instructions and perform: obtaining a medical image; obtaining a feature map and a medical image content recognition result that correspond to the medical image by using a medical image classification model, or obtaining the feature map and a lesion classification result that correspond to the medical image by using the medical classification model, the feature map including N channels, N being an integer greater than 1; generating a thermodynamic diagram corresponding to the medical image content recognition result or the lesion classification result according to the feature map and a weight parameter set, the weight parameter set including N weight parameters, the weight parameters having a correspondence with the channels; and generating an image recognition result corresponding to the medical image according to the thermodynamic diagram.

In yet another aspect, the present disclosure provides a non-transitory computer-readable storage medium storing computer program instructions executable by at least one processor to perform: obtaining a medical image; obtaining a feature map and a medical image content recognition result that correspond to the medical image by using a medical image classification model, or obtaining the feature map and a lesion classification result that correspond to the medical image by using the medical classification model, the feature map including N channels, N being an integer greater than 1; generating a thermodynamic diagram corresponding to the medical image content recognition result or the lesion classification result according to the feature map and a weight parameter set, the weight parameter set including N weight parameters, the weight parameters having a correspondence with the channels; and generating an image recognition result corresponding to the medical image according to the thermodynamic diagram.

In yet another aspect, the present disclosure provides a medical imaging system, including a probe, a circuit, a processor, and a display, the circuit being configured to excite the probe to obtain a medical image; the processor being configured to process the medical image; and the display being configured to display an image recognition result or a lesion recognition result, the processor further performing the method according to one or more of the foregoing aspects.

Embodiments of the present disclosure may deliver one or more of the following advantages:

In the embodiments of the present disclosure, a medical image recognition method is provided. A medical image is first obtained, and a feature map and a lesion classification result that correspond to the medical image are then obtained by using a medical image classification model, the feature map being obtained by convoluting the medical image by using a convolutional layer of the medical image classification model, and the feature map including N channels. A thermodynamic diagram corresponding to the lesion classification result is then generated according to the feature map and a weight parameter set, the weight parameter set including N weight parameters, and the weight parameters having a correspondence with the channels. A lesion recognition result corresponding to the medical image is finally generated according to the thermodynamic diagram. By using the foregoing manner, a discriminative region corresponding to the lesion classification result may be further visualized by using the thermodynamic diagram while the lesion classification result based on the medical image is obtained. This not only provides good interpretability for the model, but also provides a powerful basis for automatic diagnosis, so that the model is more convincing. A doctor and a patient may additionally feel more relieved when using the medical imaging system, thereby improving the reliability of diagnosis based on the medical image.

Other aspects of the present disclosure can be understood by those skilled in the art in light of the description, the claims, and the drawings of the present disclosure.

BRIEF DESCRIPTION OF THE DRAWINGS

To facilitate a better understanding of technical solutions of certain embodiments of the present disclosure, accompanying drawings are described below. The accompanying drawings are illustrative of certain embodiments of the present disclosure, and a person of ordinary skill in the art may still derive other drawings from these accompanying drawings without having to exert creative efforts. When the following descriptions are made with reference to the accompanying drawings, unless otherwise indicated, same numbers in different accompanying drawings may represent same or similar elements. In addition, the accompanying drawings are not necessarily drawn to scale.

DETAILED DESCRIPTION

Figure 1A:
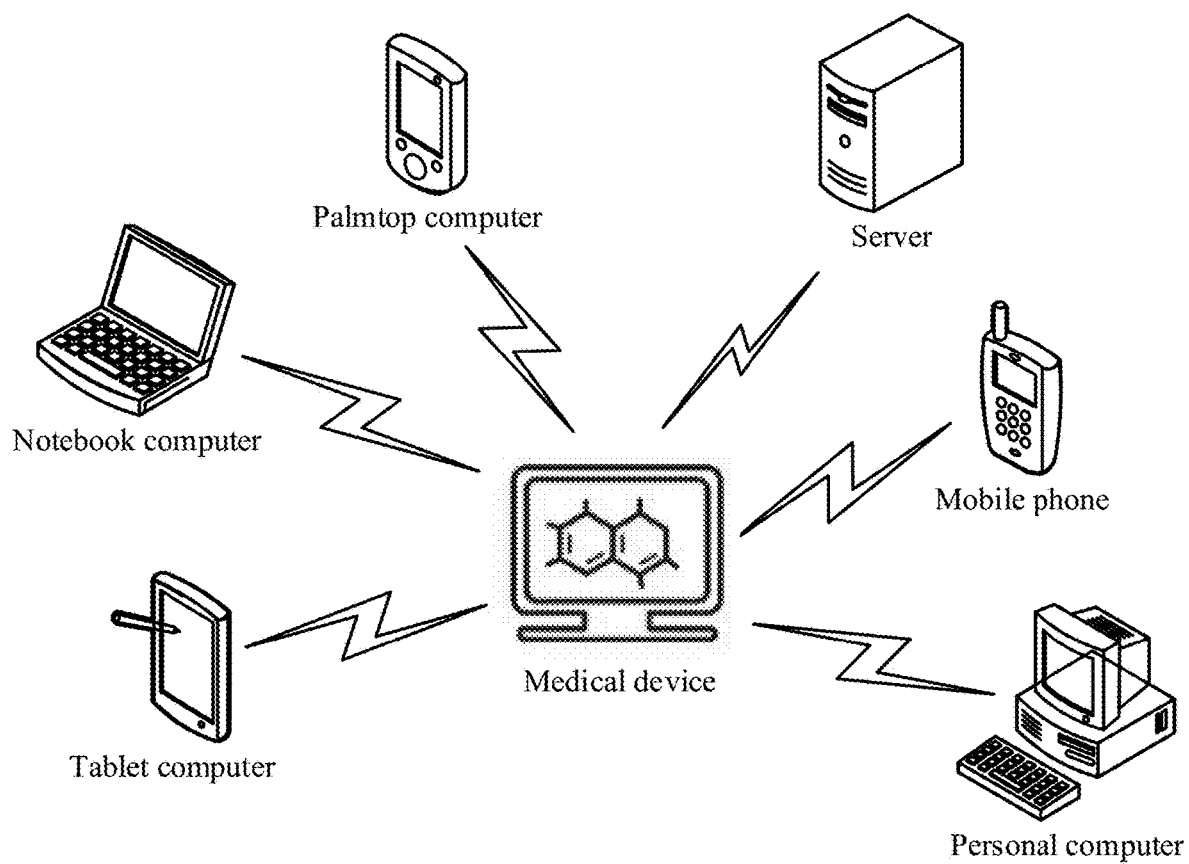
FIG. 1A is a schematic architectural diagram of a lesion recognition system according to one or more embodiments of the present disclosure.

To make objectives, technical solutions, and/or advantages of the present disclosure more comprehensible, certain embodiments of the present disclosure are further elaborated in detail with reference to the accompanying drawings. The embodiments as described are not to be construed as a limitation to the present disclosure. All other embodiments obtained by a person of ordinary skill in the art without creative efforts shall fall within the protection scope of embodiments of the present disclosure.

Throughout the description, and when applicable, "some embodiments" or "certain embodiments" describe subsets of all possible embodiments, but it may be understood that the "some embodiments" or "certain embodiments" may be the same subset or different subsets of all the possible embodiments, and can be combined with each other without conflict.

In certain embodiments, the term "based on" is employed herein interchangeably with the term "according to."

Embodiments of the present disclosure provide a medical image recognition method and apparatus, and an image recognition result presentation method and apparatus, which not only provide good interpretability for a model, but also provide a powerful basis for automatic diagnosis, so that the model is more convincing, thereby improving the reliability of diagnosis based on a medical image.

In the present disclosure, claims, and accompanying drawings of the present disclosure, the terms "first", "second", "third", "fourth", and the like (if existing) are intended to distinguish between similar objects rather than describe a specific sequence or a precedence order. Data used in this way may be interchanged in an appropriate implementation, so that the embodiments of the present disclosure described herein can be implemented in a sequence other than the sequence illustrated or described herein. In addition, the terms "include", "corresponding to" and any other variants are intended to cover the non-exclusive inclusion. For example, a process, method, system, product, or device that includes a series of steps or units is not necessarily limited to those expressly listed steps or units, but may include other steps or units not expressly listed or inherent to such a process, method, product, or device.

In certain embodiments, a medical image processing method, a medical image recognition method, and an image recognition result presentation method provided in the present disclosure are applicable to the medical field of artificial intelligence (AI), and are specifically applicable to the field of medical image recognition based on a computer vision (CV) technology. The AI is a theory, method, technology and application system that uses digital computers or machines controlled by digital computers to simulate, extend and expand human intelligence, perceive the environment, acquire knowledge, and use knowledge to obtain the best results. In other words, the AI is a comprehensive technology of computer science, which attempts to understand essence of intelligence and produces a new intelligent machine that can respond in a manner similar to human intelligence. The AI is to study the design principles and implementation methods of various intelligent machines, to enable the machines to have the functions of perception, reasoning, and decision-making.

The AI technology is a comprehensive discipline, covering a wide range of fields including both a hardware-level technology and a software-level technology. The basic AI technology generally includes a technology such as a sensor, a dedicated AI chip, cloud computing, distributed storage, a big data processing technology, an operation/interaction system, or mechatronics. An AI software technology includes fields such as a CV technology, a speech processing technology, a natural language processing technology, and machine learning/deep learning (DL).

The CV is a science that studies how to use a machine to "see", and furthermore, is machine vision that a camera and a computer are used for replacing human eyes to perform recognition, tracking, measurement, and the like on a target, and further perform graphic processing, so that the computer processes the target into an image more suitable for human eyes to observe, or an image transmitted to an instrument for detection. As a scientific subject, the CV studies related theories and technologies, and attempts to establish an AI system that can obtain information from images or multi-dimensional data. The CV technologies generally include technologies such as image processing, image recognition, image semantic understanding (ISU), image retrieval, optical character recognition (OCR), video processing, video semantic understanding, video content/behavior recognition, three-dimensional (3D) object reconstruction, a 3D technology, virtual reality, augmented reality, synchronous positioning, and map construction, and further include biological feature recognition technologies such as common face recognition and fingerprint recognition.

With the fast development of science and technologies, the AI is also increasingly widely applied to the medical industry. The most common medical images in the medical field include, but not limited to, an endoscopic image, a blood vessel image, a cardiovascular image, a computerized tomography (CT) image, a B-mode ultrasound image, and a pathological image. Because the medical image directly reflects a lesion inside the tissue, and is an important basis for a doctor to perform disease diagnosis and even a final basis for some disease diagnosis. For example, in cancer diagnosis, a doctor observes a radiographic image of a lesion, including observing whether there is a shadow, a plaque, or blood vessel dilatation. In the present disclosure, lesion recognition is performed on the endoscopic image. However, this is not to be as a limitation on the present disclosure.

The medical image is an important information entry for a doctor to know a condition of a patient. Although a high-quality medical imaging device has currently become popular, interpretation of the medical image generally requires the doctor to have a professional knowledge background and long-term experience accumulation. Considering that the population is large, the load on the medical imaging system is heavy, and experienced doctors are insufficient in quantity and are gathered in large-scale grade-A tertiary hospitals in first-tier cities, medical resources are scarce. In the method provided in the present disclosure, automatic diagnosis may be performed on the endoscopic image, and a region on which the automatic diagnosis is based may be further visualized. That is, an endoscopic lesion type is obtained by applying a DL model, and a region on which such a decision made is based may be further obtained. This basis points out the region on which the doctor may need to focus, so that the model has better interpretability and is easier to be convinced.

The method provided in the embodiments of the present disclosure may be performed by a data processing device. For ease of understanding, the present disclosure provides a medical image recognition method, and the method is applicable to a lesion recognition system shown in FIG. 1A. FIG. 1A is a schematic architectural diagram of a lesion recognition system according to an embodiment of the present disclosure. As shown in the figure, the lesion recognition system may include a medical device, and the medical device may be an endoscopic device or an electron microscope. After acquiring a to-be-recognized medical image, the medical device first performs lesion classification on the medical image, then positions a region on which the lesion classification is based, and finally combines the region with an original medical image to obtain a visualized result, to provide a region on which the focus is to a doctor. In this implementation, the data processing device is the medical device. The term "to-be-recognized medical image" may also be understood as a "medical image." In certain embodiments, the term "to-be-recognized medical image" refers to a medical image that is subject to one or more steps referenced in the method according to embodiments illustratively shown one or more of the accompanying drawings. In certain embodiments, after acquiring a medical image, the medical device may send the medical image to a terminal device, and the terminal device performs lesion classification on the medical image, then positions a region on which the lesion classification is based, finally combines the region with an original medical image to obtain a visualized result, and presents the visualized result on an interface. In this implementation, the data processing device is the terminal device. In certain embodiments, after acquiring a medical image, the medical device may send the medical image to a server, and the server performs lesion classification on the medical image, then positions a region on which the lesion classification is based, and finally combines the region with an original medical image to obtain a visualized result. The server feeds back the result to a terminal device or a medical device, and the terminal device or the medical device presents the result. In this implementation, the data processing device is the server.

The terminal device includes, but not limited to, a tablet computer, a notebook computer, a palmtop computer, a mobile phone, a speech interaction device, and a personal computer (PC), and is not limited herein.

Figure 1B:
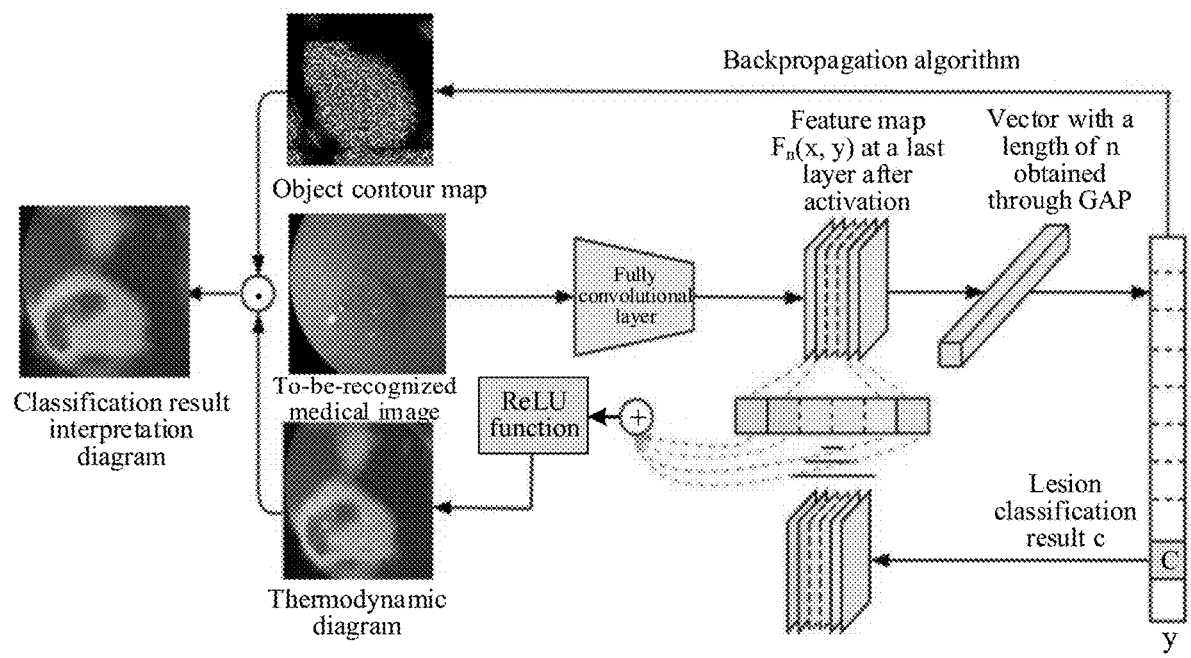
FIG. 1B is an overall schematic structural diagram of generating a lesion recognition result according to one or more embodiments of the present disclosure.

The present disclosure provides a DL-based endoscopic image automatic diagnosis solution and also provides a region of a corresponding image on which the diagnosis made is based. For ease of understanding, referring to FIG. 1B, FIG. 1B is an overall schematic structural diagram of generating a lesion recognition result according to an embodiment of the present disclosure. As shown in the figure, a medical image is first inputted to a medical image classification model. The medical image classification model is a model based on a deep convolutional neural network, and a main body is formed by stacking convolutional layers. To explain a classification result, two branches are added herein. One branch is to decompose a prediction score of the model into each region of the medical image based on a feature map outputted by a last layer of convolution, that is, to obtain a contribution of the each region of the medical image to a final prediction being a specific class. Assuming that the medical image predicts that the medical image classification model belongs to a lesion classification result c, a thermodynamic diagram corresponding to the lesion classification result c is obtained. In certain embodiments, the thermodynamic diagram is obtained through upsampling, so that the thermodynamic diagram has the same size as the medical image.

The term "medical image" may also be understood as an "image." In certain embodiments, the term "medical image" refers to an image that is subject to one or more steps referenced in the accompanying drawings.

The other branch is to obtain an object contour map by using a backpropagation algorithm (for example, a guided backpropagation algorithm). The object contour map gains a contour feature of all objects in an overall medical image, has no relationship with a specified class, and belongs to lower-level semantic information. Because the object contour map adopts convolutional network results of an input layer and previous layers, and reserves high-resolution image contour information, the object contour map has a higher resolution and is clearer. Weighted superimposition is performed on the thermodynamic diagram and the object contour map together to obtain a final classification result interpretation diagram. The classification result interpretation diagram belongs to a lesion recognition result. The lesion recognition result may further include a name, a development situation, and a recommended treatment solution of a lesion.

It can be learned that the classification result interpretation diagram may be obtained without changing the original medical image classification model. Therefore, the method provided in the present disclosure may be easily applied to a plurality of types of classification models.

Figure 2A:
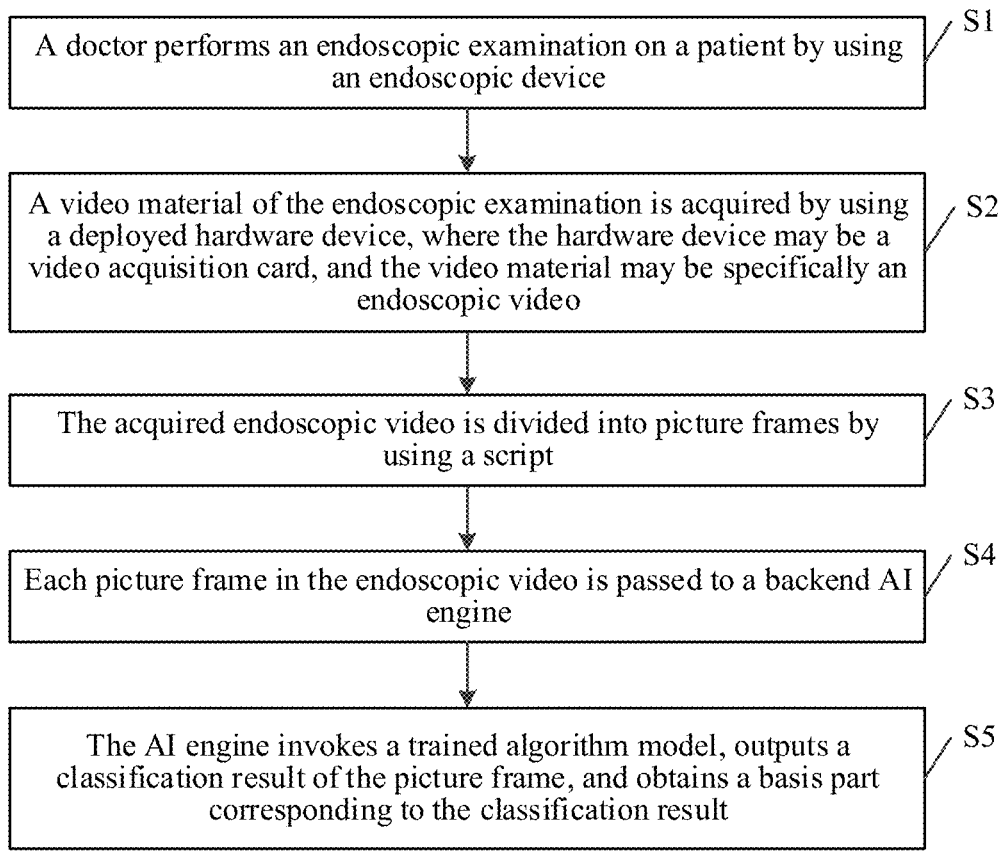
FIG. 2A is a schematic diagram of a processing procedure based on a lesion recognition system according to one or more embodiments of the present disclosure.

Based on the foregoing description, the present disclosure is further described below by using a specific product as an example. FIG. 2A is a schematic diagram of a processing procedure based on a lesion recognition system according to an embodiment of the present disclosure. As shown in the figure, at step S1, a doctor performs an endoscopic examination on a patient by using an endoscopic device; at step S2, a video material of the endoscopic examination is acquired by using a deployed hardware device, where the hardware device may be a video acquisition card, and the video material may be specifically an endoscopic video; at step S3, the acquired endoscopic video is divided into picture frames by using a script; at step S4, each picture frame in the endoscopic video is passed to a backend AI engine; and at step S5, the AI engine invokes a trained algorithm model, outputs a classification result (that is, a corresponding lesion type) of the picture frame, and obtains a basis part corresponding to the classification result (that is, outputs a thermodynamic diagram).

Figure 2B:
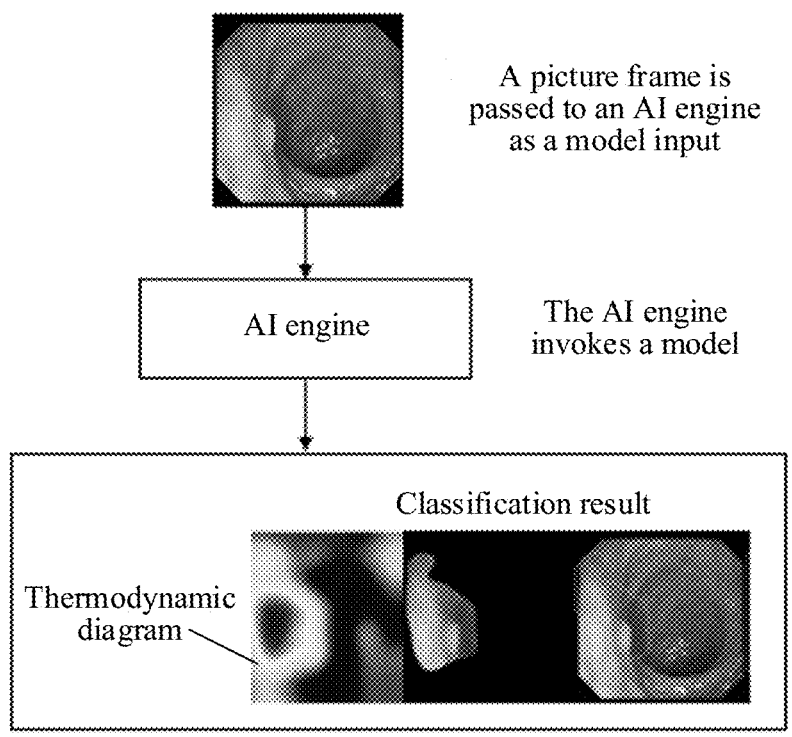
FIG. 2B is a schematic diagram of a product based on a lesion recognition system according to one or more embodiments of the present disclosure.

In the technical solutions provided in the present disclosure, the corresponding lesion type may be outputted, and a region on which the classification made by using a neural network model is based may be further outputted, to overcome disadvantages of an unexplainable neural network black box. A visualized result is given to the doctor and the patient, so that the classification product is more convincing. FIG. 2B is a schematic diagram of a product based on a lesion recognition system according to an embodiment of the present disclosure. As shown in the figure, a result returned by an AI engine includes a classification result and a thermodynamic diagram. A dark part (for example, a red part) in the thermodynamic diagram is a pixel region that has a relatively large contribution to the classification result, that is, a region on which a doctor may need to focus. To better present a visualized image to the doctor, the thermodynamic diagram may be superimposed on an original image, to help the doctor quickly position the region worthy of attention; and a threshold may be further set for the thermodynamic diagram. For example, a contour line is obtained by using 127 as the threshold, and the contour line is drawn on the original image according to the threshold and presented to the doctor. In certain embodiments, a pixel range of a red green blue (RGB) image is from 0 to 255.

The product provided in the present disclosure may assist the doctor in diagnosis and treatment. Provided that the doctor acquires a video by using a corresponding endoscopic device, the system may automatically perform framing on the video, send each frame of image to a backend AI engine, and return a lesion class and a classification basis region that correspond to the each frame of image.

Figure 3A:
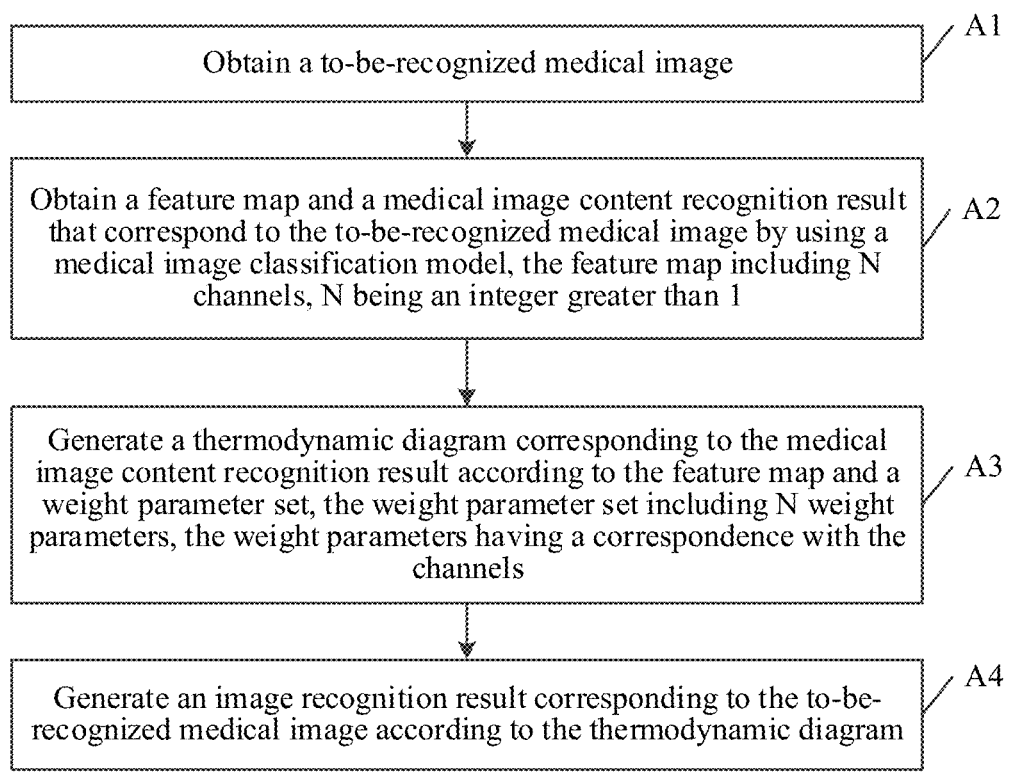
FIG. 3A is a schematic diagram of an embodiment of a medical image processing method according to one or more embodiments of the present disclosure.

With the research and progress of the AI technology, the AI technology is studied and applied to a plurality of fields, such as a common smart home, a smart wearable device, a virtual assistant, a smart speaker, smart marketing, unmanned driving, automatic driving, an unmanned aerial vehicle, a robot, smart medical care, and smart customer service. It is believed that with the development of technologies, the AI technology will be applied to more fields, and play an increasingly important role. With reference to the foregoing description, the solutions provided in the embodiments of the present disclosure involve technologies such as AI image recognition, and are specifically described by using the following embodiments. Referring to FIG. 3A, an embodiment of a medical image processing method in the embodiments of the present disclosure includes the following steps:

A1. Obtain a medical image.

In this embodiment, the medical image may be obtained by using an image recognition apparatus. The image recognition apparatus may be deployed on a terminal device, a server, or a medical device, which is not limited herein. The medical image is a medical image of a different type such as a CT image or a microscope image.

A2. Obtain a feature map and a medical image content recognition result that correspond to the medical image by using a medical image classification model, the feature map including N channels, N being an integer greater than 1. In this embodiment, the image recognition apparatus inputs the medical image to the medical image classification model, and the medical image classification model outputs the feature map and the medical image content recognition result that correspond to the medical image. In certain embodiments, the medical image classification model is a neural network based on deep convolution, such as a visual geometry group (VGG) network, a residual neural network (res-net) or a dense convolutional network (dense-net), and a main body of the medical image classification model is formed by stacking convolutional layers.

Based on this, a manner of obtaining a feature map and a medical image content recognition result that correspond to the medical image by using a medical image classification model may be obtaining the feature map corresponding to the medical image by using a convolutional layer of the medical image classification model, and processing the feature map by using a global average pooling (GAP) layer of the medical image classification model, to obtain a feature vector. Then, C class prediction scores are calculated according to the feature vector and a weight parameter set, each class prediction score being corresponding to one class, C being an integer greater than or equal to 1; and the medical image content recognition result is determined from C classes according to the C class prediction scores.

It is assumed that the inputted medical image is an RGB image, and a size of the medical image is expressed as H*W*3, for example, 224*224*3. A feature map outputted through a last convolutional layer is obtained after the medical image passes through a plurality of cascaded convolutional layers and pooling layers. In certain embodiments, each feature map extracted by using a convolution kernel includes partial spatial features of the image, and a later convolutional layer corresponds to a larger receptive field. That is, a more global semantic feature may be extracted. The feature map is represented by $F_n(x,y)$, and n in the feature map $F_n(x,y)$ represents a feature map of an nth channel. That is, n=0, 1, 2, . . . , or N−1, and a size of the feature map is expressed as X*Y*N. Assuming that the size is 7*7*1024, N=1024. (x,y) represents a spatial position in the feature map. That is, x=0, 1, 2, . . . , or X−1, and y=0, 1, 2, . . . , or Y−1.

The feature map passes through the GAP layer, that is, an average value of a feature map of each channel is obtained, to obtain a feature vector (a size of which is 1*N, for example, 1*1024). Then, the feature vector is mapped to a prediction score of each class (a size of which is 1×C, where C is a quantity of classes) through a fully-connected layer. A class with a highest score is obtained from all classes as the medical image content recognition result of the medical image.

A3. Generate a thermodynamic diagram corresponding to the medical image content recognition result according to the feature map and a weight parameter set, the weight parameter set including N weight parameters, the weight parameters having a correspondence with the channels.

In this embodiment, the image recognition apparatus generates the thermodynamic diagram corresponding to the medical image content recognition result according to the feature map and the weight parameter set, the weight parameter set including N weight parameters. That is, each channel of the feature map corresponds to one weight parameter. The weight parameter may be preset according to an empirical value or obtained through training. This is not limited herein.

For each of the C classes, one thermodynamic diagram may be obtained. In actual implementation, upsampling is performed on the thermodynamic diagram, and a size the same as that of the original image (that is, the medical image) is then obtained, to superimpose the thermodynamic diagram on the original image (that is, the medical image) for presentation, making it convenient for naked eyes to observe. A main objective of upsampling is to enlarge the image, so that the image may be displayed on a display device with a higher resolution. A principle of upsampling is to interpolate a new element between pixels based on original image pixels by using an appropriate interpolation algorithm. The interpolation algorithms include conventional interpolation, edge-based image interpolation, and region-based image interpolation.

A4. Generate an image recognition result corresponding to the medical image according to the thermodynamic diagram.

In this embodiment, the image recognition apparatus superimposes the thermodynamic diagram generated at step A3 on the original image (that is, the medical image), to generate a classification result interpretation diagram. In certain embodiments, the image recognition result may include only the classification result interpretation diagram, or include both the classification result interpretation diagram and information related to a lesion classification result such as a name of the lesion classification result, a development situation of a lesion, and related data of a patient.

In this embodiment of the present disclosure, a medical image recognition method is provided. A discriminative region corresponding to the lesion classification result may be further visualized by using the thermodynamic diagram while the lesion classification result based on the medical image is obtained. This not only provides good interpretability for the model, but also provides a powerful basis for automatic diagnosis, so that the model is more convincing. A doctor and a patient may additionally feel more relieved when using the medical imaging system, thereby improving the reliability of diagnosis based on the medical image. In certain embodiments, based on the embodiment corresponding to FIG. 3A, after a feature map and a medical image content recognition result that correspond to the medical image are obtained by using a medical image classification model, a gradient propagation result may be further obtained according to the medical image content recognition result based on a backward gradient propagation algorithm; and an object contour map corresponding to the medical image is generated according to the gradient propagation result. Correspondingly, in A4, a manner of generating an image recognition result corresponding to the medical image according to the thermodynamic diagram may be generating the image recognition result corresponding to the medical image according to the thermodynamic diagram and the object contour map.

Because the object contour map adopts convolutional network results of an input layer and previous layers, and reserves high-resolution image contour information, the object contour map has a higher resolution and is clearer, and is combined with the thermodynamic diagram to obtain a clear and visualized classification result interpretation diagram, which is conducive to more accurate diagnosis of the endoscopic image.

A manner of obtaining a gradient propagation result according to the medical image content recognition result based on a backward gradient propagation algorithm may be obtaining the gradient propagation result according to the medical image content recognition result based on a guided backpropagation algorithm, the guided backpropagation algorithm being used for back passing a feature corresponding to a position in which both a gradient and an input value are greater than 0.

In the foregoing manner, a gradient corresponding to a position in which both an input value and the gradient are greater than 0 may be back passed. Therefore, there are fewer gradients back passed based on the guided backpropagation algorithm, and pixels that are more sensitive to the class are activated, so that a final object contour map is clearer and more vivid.

Figure 3B:
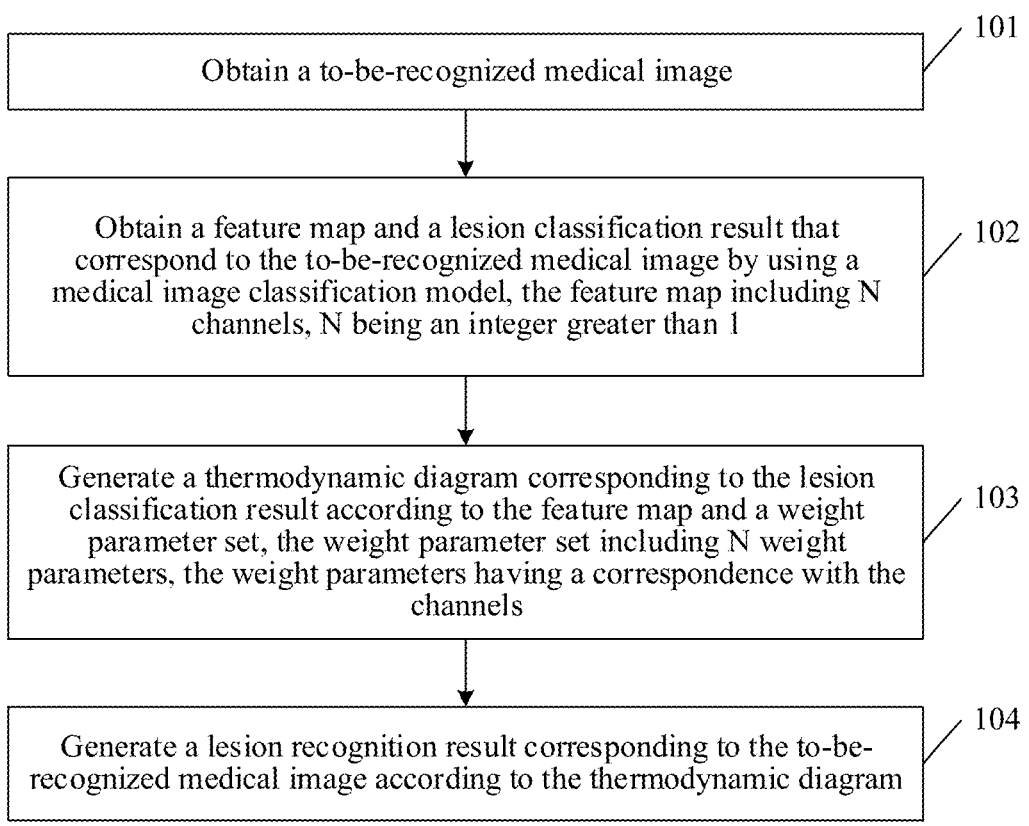
FIG. 3B is a schematic diagram of an embodiment of a medical image recognition method according to one or more embodiments of the present disclosure.

With reference to the foregoing description, the solutions provided in the embodiments of the present disclosure involve technologies such as AI image recognition, and are specifically described by using the following embodiments. Referring to FIG. 3B, an embodiment of a medical image recognition method in the embodiments of the present disclosure includes the following steps:

101. Obtain a medical image.

In this embodiment, the image recognition apparatus obtains the medical image. The image recognition apparatus may be deployed on a terminal device, a server, or a medical device, which is not limited herein. The medical image is specifically an endoscopic image. The endoscopic images involved in the present disclosure include, but not limited to, an endoscopic image of a gastrointestinal tract, an endoscopic image of a pancreas, an endoscopic image of a biliary tract, an endoscopic image of a respiratory tract, and an endoscopic image of a urinary tract.

102. Obtain a feature map and a lesion classification result that correspond to the medical image by using a medical image classification model, the feature map including N channels, N being an integer greater than 1.

In this embodiment, the image recognition apparatus inputs the medical image to the medical image classification model, and the medical image classification model outputs the lesion classification result corresponding to the medical image. In addition, in the process of outputting the lesion classification result, the feature map may be outputted after the medical image passes through a plurality of cascaded convolutional layers. In certain embodiments, the medical image classification model is a neural network based on deep convolution, such as a VGG network, a res-net or a dense-net, and a main body of the medical image classification model is formed by stacking convolutional layers.

Specifically, it is assumed that the inputted medical image is an RGB image, and a size of the medical image is expressed as H*W*3, for example, 224*224*3. A feature map outputted through a last convolutional layer is obtained after the medical image passes through a plurality of cascaded convolutional layers and pooling layers. In certain embodiments, each feature map extracted by using a convolution kernel includes partial spatial features of the image, and a later convolutional layer corresponds to a larger receptive field. That is, a more global semantic feature may be extracted. The feature map is represented by $F_n(x,y)$, and n in the feature map $F_n(x,y)$ represents a feature map of an nth channel. That is, $n=0, 1, 2, \ldots$, or $N-1$, and a size of the feature map is expressed as X*Y*N. Assuming that the size is 7*7*1024, N=1024. (x,y) represents a spatial position in the feature map. That is, $x=0, 1, 2, \ldots$, or $X-1$, and $y=0, 1, 2, \ldots$, or $Y-1$.

The feature map passes through the GAP layer, that is, an average value of a feature map of each channel is obtained, to obtain a vector (a size of which is 1*N, for example, 1*1024). Then, the vector is mapped to a prediction score of each class (a size of which is 1×C, where C is a quantity of classes) through a fully-connected layer. A class with a highest score is obtained from all classes as the lesion classification result of the medical image.

Classes of a small intestine are used as an example. The classes include, but not limited to, a small intestine tumor, a smooth muscle tumor, a sarcoma, a polyp, a lymphoma, and an inflammation.

103. Generate a thermodynamic diagram corresponding to the lesion classification result according to the feature map and a weight parameter set, the weight parameter set including N weight parameters, the weight parameters having a correspondence with the channels.

In this embodiment, the image recognition apparatus generates the thermodynamic diagram corresponding to the lesion classification result according to the feature map and the weight parameter set, the weight parameter set including N weight parameters. That is, each channel of the feature map corresponds to one weight parameter. The weight parameter may be preset according to an empirical value or obtained through training. This is not limited herein.

Figure 4:
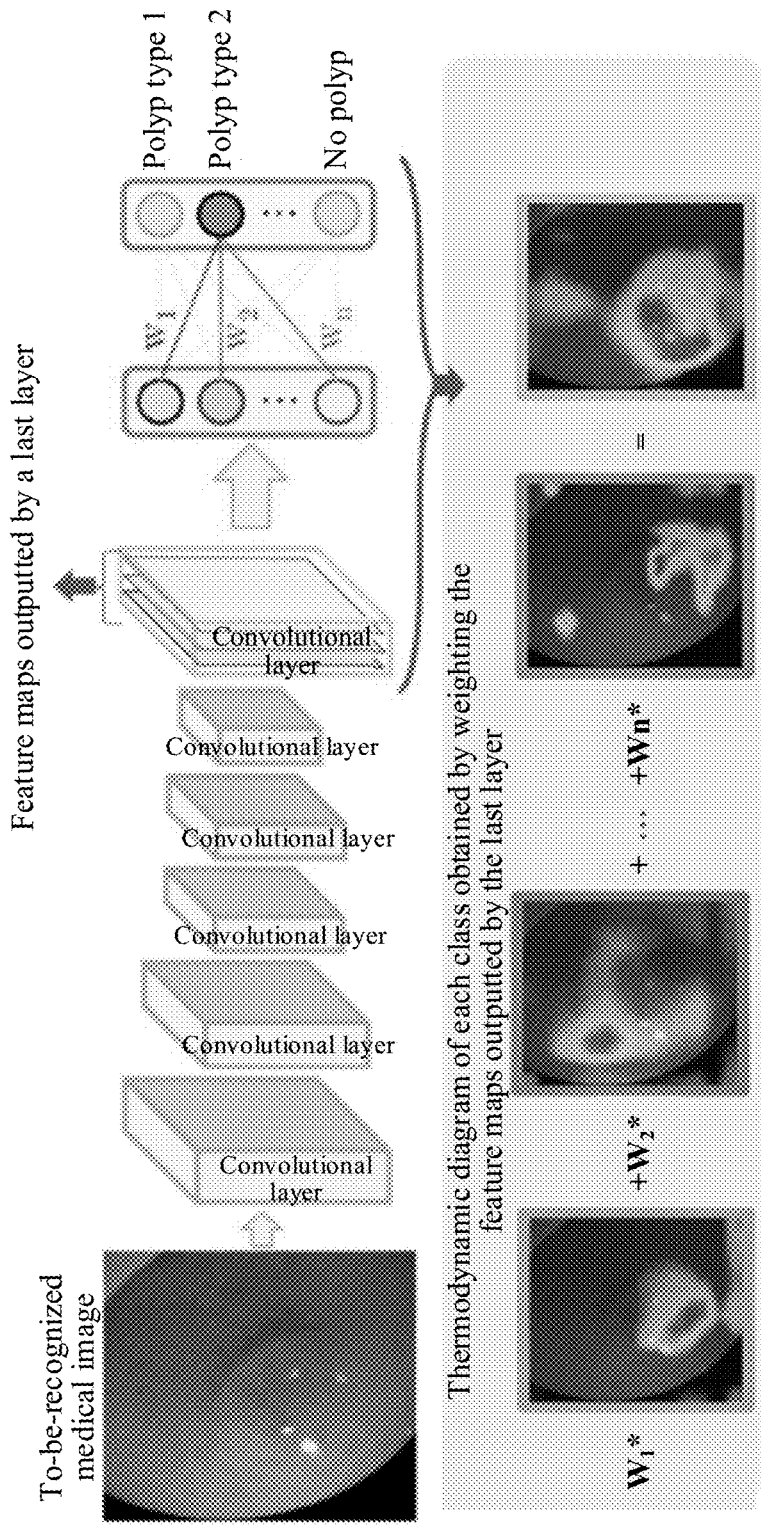
FIG. 4 is a schematic flowchart of generating a thermodynamic diagram according to one or more embodiments of the present disclosure.

For each of the C classes, one thermodynamic diagram may be obtained. For ease of description, referring to FIG. 4, FIG. 4 is a schematic flowchart of generating a thermodynamic diagram according to an embodiment of the present disclosure. As shown in the figure, description is made by using an example in which a class is a "polyp type 2" under colonoscopy. The medical image is inputted to a plurality of convolutional layers, a last convolutional layer outputs feature maps, a thermodynamic diagram is obtained by weighting the feature maps at the last layer (for example, respectively multiplying by weight parameters W1, W2, . . . , and Wn) and performing summation, and the thermodynamic diagram is superimposed on the original image (that is, the medical image), which indicates a region in the medical image that determines a final predicted polyp type 2. A highlighted region in the thermodynamic diagram coincides with a lesion (an elliptical convex polyp), which indicates that the model not only has a correct prediction, but also has a correct prediction basis region.

In actual implementation, upsampling is performed on the thermodynamic diagram, and a size the same as that of the original image (that is, the medical image) is then obtained, to superimpose the thermodynamic diagram on the original image (that is, the medical image) for presentation, making it convenient for naked eyes to observe. A main objective of upsampling is to enlarge the image, so that the image may be displayed on a display device with a higher resolution. A principle of upsampling is to interpolate a new element between pixels based on original image pixels by using an appropriate interpolation algorithm. The interpolation algorithms include conventional interpolation, edge-based image interpolation, and region-based image interpolation.

Figure 5:
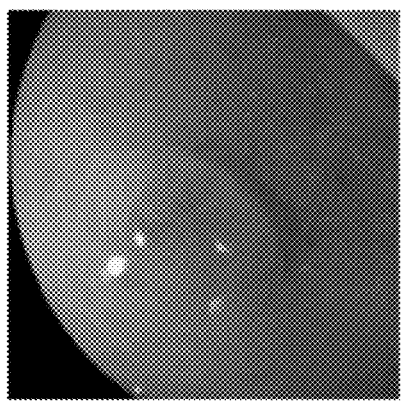
FIG. 5 is a schematic diagram of an embodiment of generating a thermodynamic diagram based on a lesion classification result according to one or more embodiments of the present disclosure.
Figure 5:
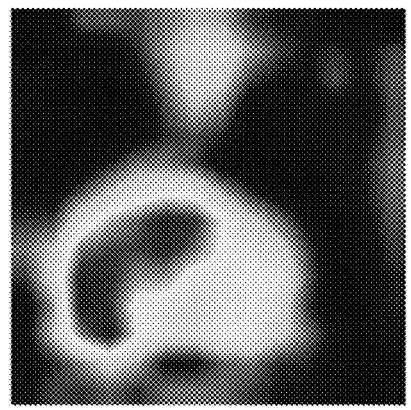

For ease of description, referring to FIG. 5, FIG. 5 is a schematic diagram of an embodiment of generating a thermodynamic diagram based on a lesion classification result according to an embodiment of the present disclosure. As shown in the figure, a diagram (a) in FIG. 5 is an original image, that is, a medical image; a diagram (b) in FIG. 5 is a thermodynamic diagram corresponding to the medical image. The diagram (a) and the diagram (b) are superimposed to obtain a classification result interpretation diagram.

104. Generate a lesion recognition result corresponding to the medical image according to the thermodynamic diagram.

In this embodiment, the image recognition apparatus superimposes the thermodynamic diagram generated at step 103 on the original image (that is, the medical image) to generate the classification result interpretation diagram. In certain embodiments, the lesion recognition result may include only the classification result interpretation diagram, or include both the classification result interpretation diagram and information related to a lesion classification result such as a name of the lesion classification result, a development situation of a lesion, and related data of a patient.

In the embodiments of the present disclosure, a medical image recognition method is provided. A medical image is first obtained, and a feature map and a lesion classification result that correspond to the medical image are then obtained by using a medical image classification model, the feature map being obtained by convoluting the medical image by using a convolutional layer of the medical image classification model, and the feature map including N channels. A thermodynamic diagram corresponding to the lesion classification result is then generated according to the feature map and a weight parameter set, the weight parameter set including N weight parameters, and the weight parameters having a correspondence with the channels. A lesion recognition result corresponding to the medical image is finally generated according to the thermodynamic diagram. By using the foregoing manner, a discriminative region corresponding to the lesion classification result may be further visualized by using the thermodynamic diagram while the lesion classification result based on the medical image is obtained. This not only provides good interpretability for the model, but also provides a powerful basis for automatic diagnosis, so that the model is more convincing. A doctor and a patient may additionally feel more relieved when using the medical imaging system, thereby improving the reliability of diagnosis based on the medical image.

In certain embodiments, based on the embodiment corresponding to FIG. 3B, after the obtaining a feature map and a lesion classification result that correspond to the medical image by using a medical image classification model, the method may further include: obtaining a gradient propagation result according to the lesion classification result based on a backward gradient propagation algorithm; and generating an object contour map corresponding to the medical image according to the gradient propagation result; and the generating a lesion recognition result corresponding to the medical image according to the thermodynamic diagram may include: generating a lesion recognition result corresponding to the medical image according to the thermodynamic diagram and the object contour map.

In this embodiment, a method for generating a lesion recognition result based on the thermodynamic diagram and the object contour map is described. In a manner of step 101 to step 104, a thermodynamic diagram corresponding to the medical image in each class may be predicted, and the thermodynamic diagram may well distinguish different classes of discriminative regions. However, the thermodynamic diagram has a relatively low resolution and a less obvious contour. To obtain a higher-definition image, another branch is introduced to the present disclosure. That is, an object contour map corresponding to the medical image is generated by using a backward gradient propagation algorithm. For ease of description, referring to FIG. 6, FIG. 6 is a schematic diagram of an embodiment of generating an object contour map based on a lesion classification result according to an embodiment of the present disclosure.

Figure 6:
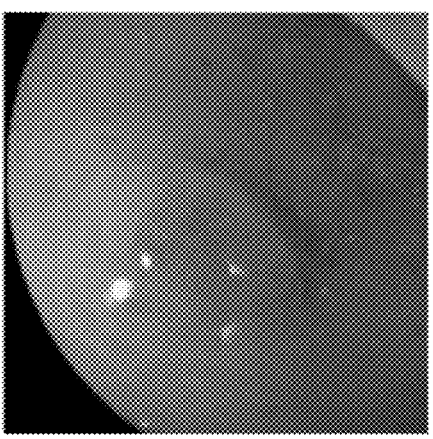
FIG. 6 is a schematic diagram of an embodiment of generating an object contour map based on a lesion classification result according to one or more embodiments of the present disclosure.
Figure 6:
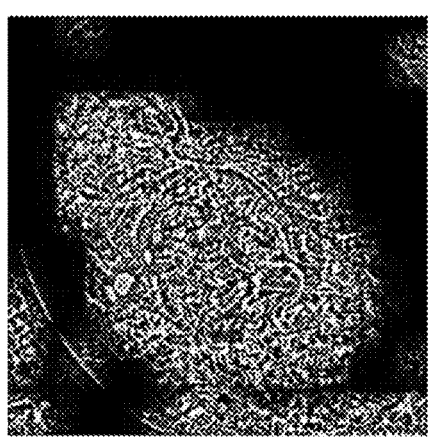
Figure 7:
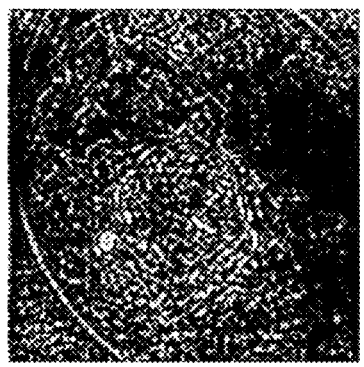
FIG. 7 is a schematic diagram of an embodiment of generating a classification result interpretation diagram according to one or more embodiments of the present disclosure.
Figure 7:
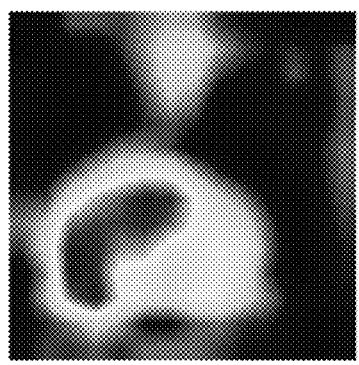
Figure 7:
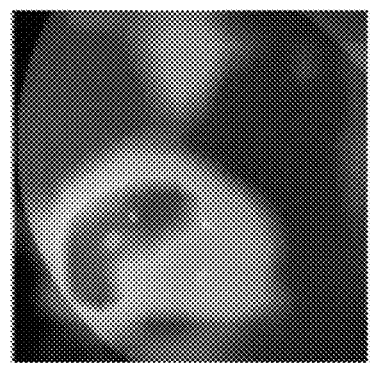

As shown in the figure, a diagram (a) in FIG. 6 is an original image, that is, the medical image; a diagram (b) in FIG. 6 is the object contour map corresponding to the medical image. The diagram (a) and the diagram (b) are superimposed to obtain a classification result interpretation diagram. Further, to better reflect a fusion process of the object contour map and the thermodynamic diagram, referring to FIG. 7, FIG. 7 is a schematic diagram of an embodiment of generating a classification result interpretation diagram according to an embodiment of the present disclosure. As shown in the figure, a diagram (a) in FIG. 7 is a probability diagram corresponding to a medical image, that is, an object contour map; a diagram (b) in FIG. 7 is a thermodynamic diagram corresponding to the medical image; a diagram (c) in FIG. 7 is a classification result interpretation diagram obtained by multiplying pixels of the object contour map by pixels of the thermodynamic diagram point by point. Therefore, high-level semantic information (that is, the thermodynamic diagram) is combined with low-level semantic information (that is, the object contour map).

Further, in this embodiment of the present disclosure, a method for generating a lesion recognition result based on the thermodynamic diagram and the object contour map is provided. That is, a gradient propagation result is first obtained according to a lesion classification result based on a backward gradient propagation algorithm, the object contour map corresponding to the medical image is then generated according to the gradient propagation result, and the lesion recognition result is finally generated based on the thermodynamic diagram and the object contour map. In the foregoing manner, another branch is provided. That is, one object contour map is obtained by using the backward gradient propagation algorithm. The object contour map gains a contour feature of all objects in an overall image. Because the object contour map adopts convolutional network results of an input layer and previous layers, and reserves high-resolution image contour information, the object contour map has a higher resolution and is clearer, and is combined with the thermodynamic diagram to obtain a clear and visualized classification result interpretation diagram, which is conducive to more accurate diagnosis of the endoscopic image.

In certain embodiments, based on the first embodiment corresponding to FIG. 3B, the obtaining a feature map and a lesion classification result that correspond to the medical image by using a medical image classification model may include: obtaining the feature map corresponding to the medical image by using a convolutional layer of the medical image classification model; processing the feature map by using a GAP layer of the medical image classification model, to obtain a feature vector; calculating C class prediction scores according to the feature vector and the weight parameter set, each class prediction score being corresponding to one class, C being an integer greater than or equal to 1; and determining the lesion classification result from C classes according to the C class prediction scores.

In this embodiment, a method for determining a lesion classification result is described. For each of a total of C classes, one thermodynamic diagram may be obtained. To more accurately position the lesion, one of the C classes may be selected as the lesion classification result.

It is assumed that the feature map corresponding to the medical image is $F_n(x,y)$, and n in the feature map $F_n(x,y)$ represents a feature map of an nth channel. That is, n=0, 1, 2, . . . , or (x,y) N−1, and a size of the feature map is expressed as X*Y*N. (x,y) represents a spatial position in the feature map. That is, x=0, 1, 2, . . . , or X−1, and y=0, 1, 2, ..., or Y−1. The feature map passes through the GAP layer. That is, an average value of a feature map of each channel is obtained, to obtain a feature vector, and a size of the feature vector is 1*N. Based on the weight parameter set, the feature vector is mapped to a prediction score of each class through the fully-connected layer. That is, C class prediction scores are obtained, and a size is 1*C. For example, the medical image is an endoscopic image, and normality, an inflammation, and a cancer may need to be obtained through classification. Therefore, C=3. The cth class prediction score is represented by $Y_c$, where c=0, 1, ..., or C−1. Finally, a class with a highest score is obtained from the C class prediction scores as the lesion classification result predicted on the medical image.

Figure 8:
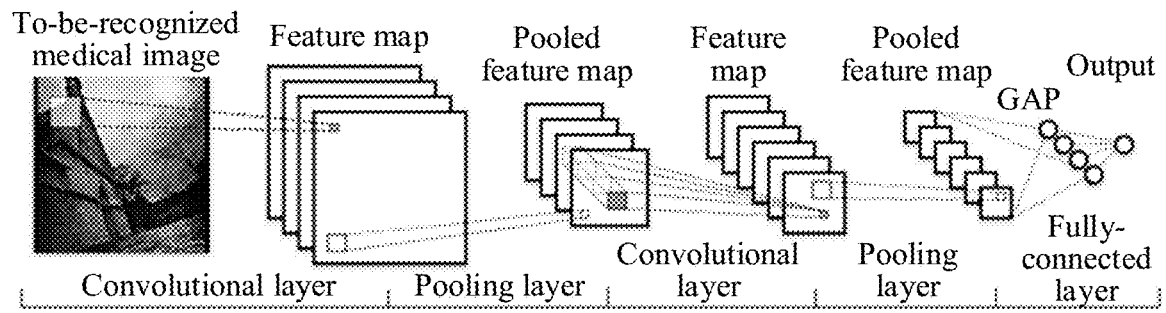
FIG. 8 is a schematic structural diagram of a medical image classification model according to one or more embodiments of the present disclosure.

For ease of understanding, referring to FIG. 8, FIG. 8 is a schematic structural diagram of a medical image classification model according to an embodiment of the present disclosure. As shown in the figure, specifically, a medical image is first inputted, a convolution operation is performed by using a convolutional layer, and features from a lower level to a higher level are extracted to obtain a feature map, thereby digging a local correlation property and a spatial invariance property of the medical image. The convolutional layer plays an important role in the medical image classification model, that is, performs abstraction and extraction on features. A downsampling operation is then performed through a pooling layer, to filter out some unimportant high-frequency information. A pooling operation is performed after the convolution operation, and plays a role in feature fusion and dimension reduction. Because spatial information is erased by a last GAP layer, a 3D matrix is transformed into a vector, that is, a feature vector is outputted. To explain the classification result and decompose a final prediction to be positioned in each region in the medical image, a last convolutional layer before the GAP layer may need to be used.

In certain embodiments, the structure of the medical image classification model in FIG. 8 is merely an example. A network structure, a training method, an optimizer type, a data enhancement method, a preprocessing method, and a regularization method for the medical image classification model are not limited in the present disclosure.

Further, in this embodiment of the present disclosure, a method for determining a lesion classification result is provided. That is, a feature map corresponding to the medical image is first obtained by using a convolutional layer, a feature vector is then obtained by using a pooling layer, and a highest score is finally selected from scores in classes as the lesion classification result according to the feature vector and a weight parameter set. In the foregoing manner, a lesion classification result of the medical image may be determined, to more accurately position the class, thereby improving the reliability and accuracy of the solutions.

In certain embodiments, based on the second embodiment corresponding to FIG. 3B, the calculating C class prediction scores according to the feature vector and the weight parameter set may include: calculating the class prediction score in the following manner:

$$Y_c = \sum_n w_n^c \sum_{(x,y)} F_n(x, y),$$

where $Y_c$ represents a class prediction score corresponding to a class, C represents a total quantity of classes, $F_n(x,y)$ represents a feature map of an channel, (x,y) represents a spatial position in the feature map, and $w_n^c$ represents a weight parameter of the feature map of the $n^{th}$ channel on a prediction being the $c^{th}$ class.

In this embodiment, a specific manner of calculating a class prediction score is described. A final outputted prediction being a class prediction score corresponding to the $c^{th}$ class is expresses as:

$$Y_c = \sum_n w_n^c \sum_{(x,y)} F_n(x, y), \text{ where } \sum_{(x,y)} F_n(x, y)$$

is obtained by using a GAP layer, $$\sum_n w_n^c \sum_{(x,y)} F_n(x, y)$$

is then obtained by using a fully-connected layer, and neurons of an input layer of the fully-connected layer are all connected to neurons of a hidden layer. One function of the fully-connected layer is to remove spatial information (a quantity of channels), which is a process of transforming a 3D matrix into a vector, that is, a full convolution operation.

Further, in this embodiment of the present disclosure, a specific manner of calculating a class prediction score is provided. In the foregoing manner, a feasible basis is provided for the implementation of the solution, thereby improving the operability of the solution.

In certain embodiments, based on the embodiment corresponding to FIG. 3B, the generating a thermodynamic diagram corresponding to the lesion classification result according to the feature map and a weight parameter set may include: generating the thermodynamic diagram in the following manner:

$$P_c(x, y) = \sum_n w_n^c F_n(x, y),$$

where $P_c(x,y)$ represents a thermodynamic diagram corresponding to a $c^{th}$ class, the thermodynamic diagram is obtained through upsampling, $F_n(x,y)$ represents a feature map of an $n^{th}$ channel, (x,y) represents a spatial position in the feature map, $w_n^c$ represents a weight parameter of the feature map of the $n^{th}$ channel on a prediction being the $c^{th}$ class, and the $c^{th}$ class belongs to the lesion classification result.

In this embodiment, a specific manner of generating a thermodynamic diagram is described. The following deduction may be performed based on an expression of the foregoing class prediction score:

$$Y_c = $$

$$\sum_n w_n^c \sum_{(x,y)} F_n(x, y) = \sum_n \sum_{(x,y)} w_n^c F_n(x, y) = \sum_{(x,y)} \sum_n w_n^c F_n(x, y) = \sum_{(x,y)} P_c(x, y),$$

That is, $$P_c(x, y) = \sum_n w_n^c F_n(x, y).$$

$w_n^c$ represents a weight parameter of a feature map of an $n^{th}$ channel on a prediction being a $c^{th}$ class, that is, a contribution of the feature map of the $n^{th}$ channel to the prediction being the $c^{th}$ class. It can be learned from the foregoing expression that a final predicted class prediction score $Y_c$ corresponding to the $c^{th}$ class may be decomposed into each local region. In other words, a larger value at each position of $P_c(x,y)$ indicates a larger contribution of a corresponding region on the medical image to the classification prediction. Therefore, $P_c(x,y)$ may be considered as the thermodynamic diagram of the prediction classification.

$$P_c(x, y) = \sum_n w_n^c F_n(x, y)$$

may be obtained by weighting a feature map $F_n(x,y)$ outputted by a last convolutional layer with a trained weight parameter $w_n^c$ and performing summation. It can be learned that a size of the thermodynamic diagram $P_c(x,y)$ is the same as a size of the feature map $F_n(x,y)$ at the last layer.

Further, in this embodiment of the present disclosure, a specific manner of generating a thermodynamic diagram is provided. In the foregoing manner, a feasible basis is provided for the implementation of the solution, thereby improving the operability of the solution.

In certain embodiments, based on the first embodiment corresponding to FIG. 3B, the obtaining a gradient propagation result according to the lesion classification result based on a backward gradient propagation algorithm may include: obtaining the gradient propagation result according to the lesion classification result based on a guided backpropagation algorithm, the guided backpropagation algorithm being used for back passing a feature corresponding to a position in which both a gradient and an input value are greater than 0.

Figure 9:
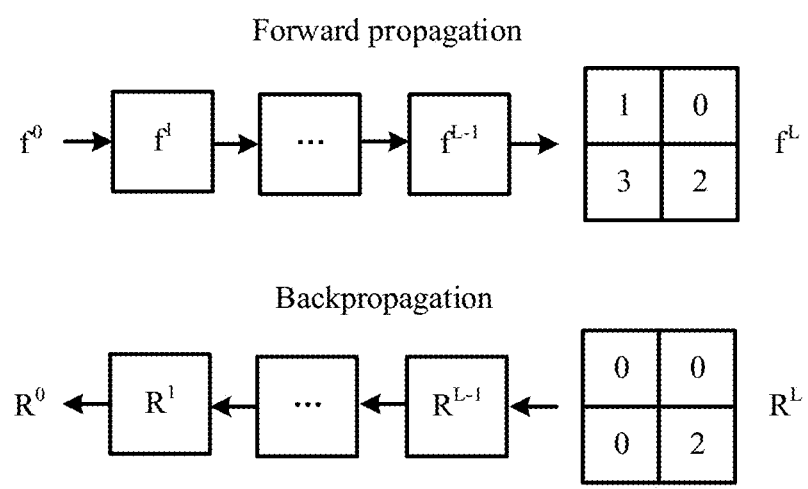
FIG. 9 is a schematic diagram of a comparison between forward propagation and backpropagation according to one or more embodiments of the present disclosure.

In this embodiment, a method for generating a gradient propagation result by using the guided backpropagation algorithm is described. First, forward propagation and backpropagation are described with reference to FIG. 9. FIG. 9 is a schematic diagram of a comparison between forward propagation and backpropagation according to an embodiment of the present disclosure. As shown in the figure, a deep learning network obtains a final label from an input image through forward propagation, and trains a network by using a backpropagation idea and a gradient descent method, to minimize a difference between a predicted label and a true label of the network. In the forward propagation, along a direction from an input to an output of the neural network, an initial input image is $f^0$, and a feature map $f^L$ is obtained after the initial input image passes through an L-layer network.

In the backpropagation, along a direction from the output to the input of the neural network, a feature map is $R^L$, and an image $R^0$ is obtained after the feature map passes through the L-layer network. A derivative of a loss function with respect to each parameter may be conveniently obtained by using the backpropagation algorithm, where a basic principle is a chain rule during derivation, and the obtained derivative is used for model training and optimization in the gradient descent method.

Figure 10:
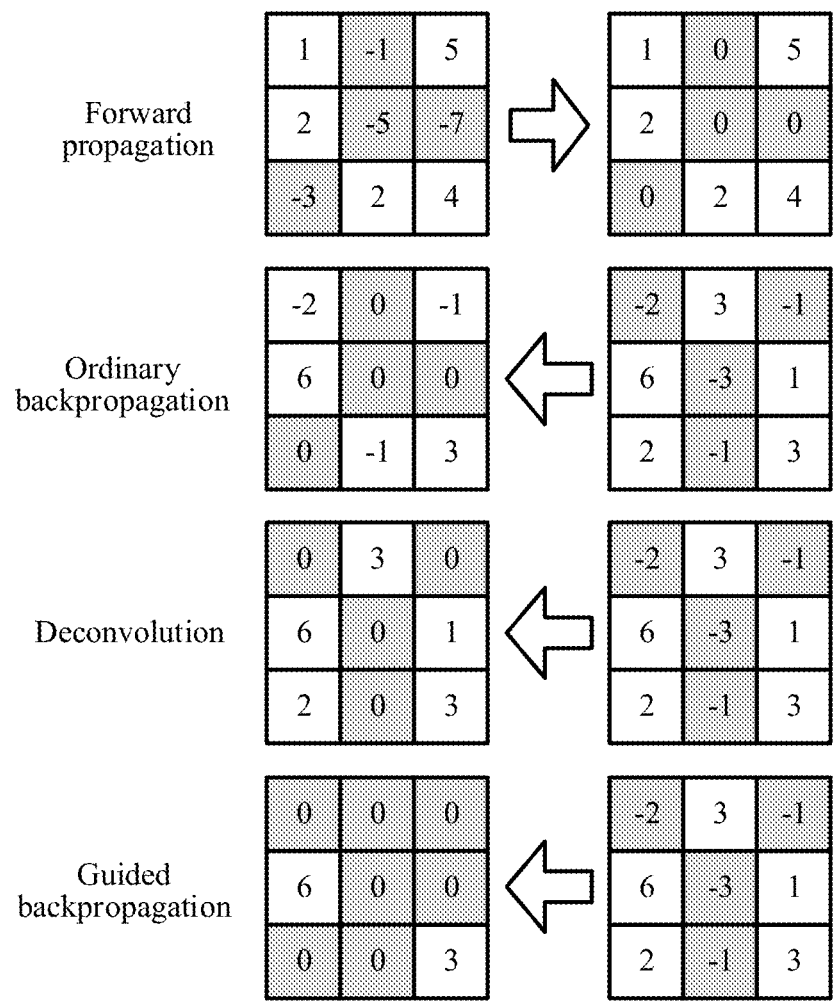
FIG. 10 is a schematic diagram of a comparison between four types of propagation algorithms according to one or more embodiments of the present disclosure.

According to the foregoing description, an ordinary backpropagation algorithm, a deconvolution algorithm, or a guided backpropagation algorithm may be used in the present disclosure to obtain a gradient propagation result, where the guided backpropagation algorithm can obtain a more vivid object contour map than an ordinary gradient-based method and a transposed convolution method. For ease of description, referring to FIG. 10, FIG. 10 is a schematic diagram of a comparison between four types of propagation algorithms according to an embodiment of the present disclosure. As shown in the figure, a process of forward propagation is forward propagating a gradient corresponding to a position in which an input value is greater than 0. A process of ordinary backpropagation is back passing a gradient corresponding to a position in which an input value is greater than 0. A process of deconvolution is back passing a gradient corresponding to a position in which the gradient is greater than 0. A process of guided backpropagation is back passing a gradient corresponding to a position in which both an input value and the gradient are greater than 0.

For example, $f_i^l$ represents an output of an $i^{th}$ layer, and an activation result obtained after the output passes through a pooling function is $f_i^{l+1} = \text{Relu}(f_i^l) = \max(f_i^l, 0)$. An ordinary backpropagation algorithm is to back pass a gradient corresponding to a position in which an input value is greater than 0, that is, $R_i^l = (f_i^l \geq 0) \cdot R_i^{l+1}$, where $$R_i^{l+1} = \frac{\partial f^{out}}{\partial f^{l+1}}.$$

A guided backpropagation function is to back pass a gradient corresponding to a position in which both an input value and the gradient are greater than 0, that is, $R_i^l = (f_i^l \geq 0) \cdot (R_i^{l+1} \geq 0) \cdot R_i^{l+1}$. A gradient propagation result obtained after the guided backpropagation is an object contour map $G_c(x,y)$ that has the same size as an original image (that is, a medical image) and has no relationship with a class. The object contour map $G_c(x,y)$ includes object information aligned with a resolution of the original image (that is, the medical image).

In certain embodiments, the pooling functions include, but not limited to, a rectified linear unit (ReLU) function, a sigmoid function, and a hyperbolic tangent (tan h) function.

Further, in this embodiment of the present disclosure, a method for obtaining a gradient propagation result based on the guided backpropagation algorithm is provided. In the foregoing manner, a gradient corresponding to a position in which both an input value and the gradient are greater than 0 may be back passed. Therefore, there are fewer gradients back passed based on the guided backpropagation algorithm, and pixels that are more sensitive to the class are activated, so that a final object contour map is clearer and more vivid.

In certain embodiments, based on the first embodiment corresponding to FIG. 3B, the generating a lesion recognition result corresponding to the medical image according to the thermodynamic diagram and the object contour map may include: generating the lesion recognition result by using the following method: $F_n(x,y)$ $\text{Visual}_c(x,y) = G_c(x,y) \odot P_c(x,y)$, where $\text{Visual}_c(x,y)$ represents a lesion recognition result corresponding to a $c^{th}$ class, $G_c(x,y)$ represents an object contour map corresponding to the $c^{th}$ class, $P_c(x,y)$ represents a thermodynamic diagram corresponding to the $c^{th}$ class, the thermodynamic diagram is obtained through upsampling, and the $c^{th}$ class belongs to the lesion classification result.

In this embodiment, an implementation of generating a lesion recognition result is described. Rough positioning of different classes may be obtained based on the thermodynamic diagram, and a high-resolution and fine-grained visualized object contour map may be obtained based on the guided backpropagation algorithm. In the present disclosure, a final clearer classification result interpretation diagram may be obtained by point by point multiplying pixels of the thermodynamic diagram obtained through upsampling by pixels of the object contour map obtained through the guided backpropagation. In certain embodiments, when the lesion recognition result is the classification result interpretation diagram, the generated $Visual_c(x,y)$ represents the lesion recognition result. If the lesion recognition result further includes other information, $Visual_c(x,y)$ represents the classification result interpretation diagram.

In this way, the high-level semantic information having a discriminative ability may be combined with low-level image information, to obtain a visualized image with both class interpretability and clarity.

Further, in this embodiment of the present disclosure, an implementation of generating a lesion recognition result is provided. In the foregoing manner, a feasible basis is provided for the implementation of the solution, thereby improving the operability of the solution.

Figure 11A:
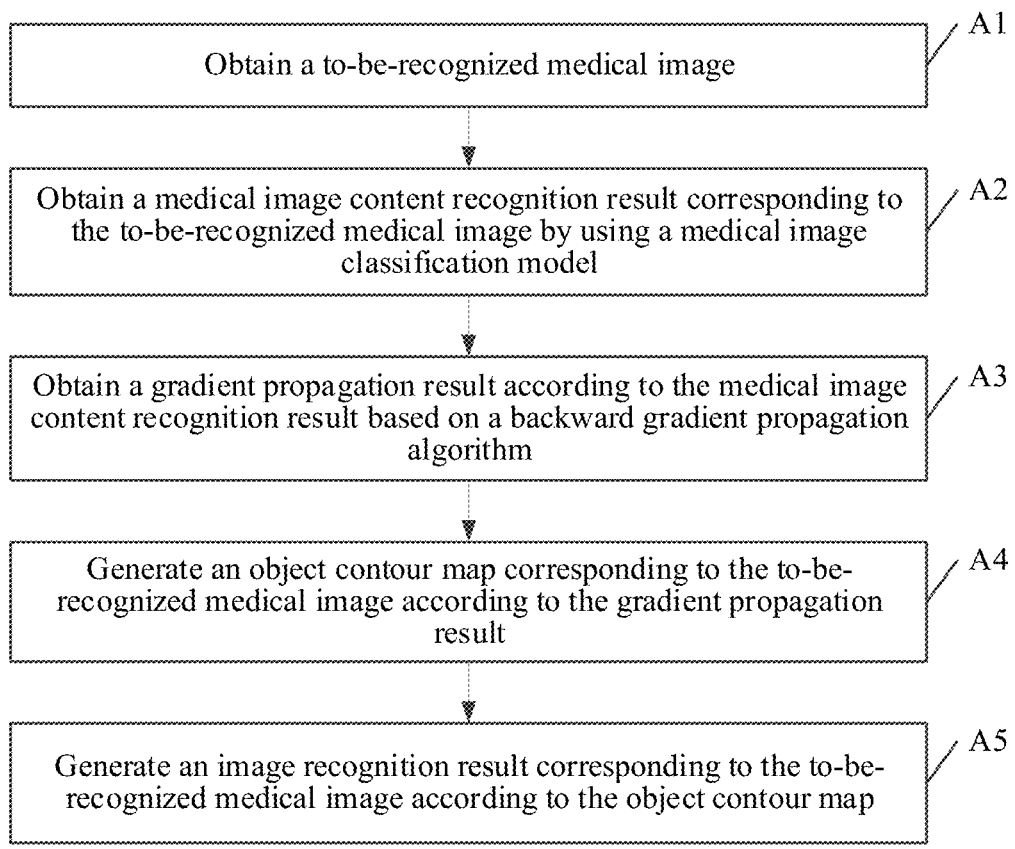
FIG. 11A is a schematic diagram of another embodiment of a medical image processing method according to one or more embodiments of the present disclosure.

With reference to the foregoing description, the solutions provided in the embodiments of the present disclosure involve technologies such as AI image recognition, and are specifically described by using the following embodiments. Referring to FIG. 11A, an embodiment of a medical image processing method in the embodiments of the present disclosure includes the following steps:

A1. Obtain a medical image.

A2. Obtain a medical image content recognition result corresponding to the medical image by using a medical image classification model.

A3. Obtain a gradient propagation result according to the medical image content recognition result based on a backward gradient propagation algorithm.

In this embodiment, the image recognition apparatus obtains the gradient propagation result according to a lesion classification result by using the backward gradient propagation algorithm. For example, the backward gradient propagation algorithm herein may be a guided backpropagation algorithm. For an implementation of obtaining a gradient propagation result according to the medical image content recognition result based on a backward gradient propagation algorithm, reference may be made to the foregoing description. Details are not described herein again.

A4. Generate an object contour map corresponding to the medical image according to the gradient propagation result.

In this embodiment, the image recognition apparatus generates the object contour map corresponding to the medical image by using the gradient propagation result. In certain embodiments, for a manner of generating, by the image recognition apparatus, the object contour map, reference may be made to the foregoing embodiments. Details are not described herein again.

A5. Generate an image recognition result corresponding to the medical image according to the object contour map.

In this embodiment, the image recognition apparatus superimposes the object contour map generated at step A4 on the original image (that is, the medical image) to generate a classification result interpretation diagram. In certain embodiments, the lesion recognition result may include only the classification result interpretation diagram, or include both the classification result interpretation diagram and information related to a lesion classification result such as a name of the lesion classification result, a development situation of a lesion, and related data of a patient.

In this embodiment of the present disclosure, a medical image recognition method is provided. A lesion classification result based on the medical image is obtained, and an object contour map may be further obtained. The object contour map gains a contour feature of all objects in an overall image. Because the object contour map adopts convolutional network results of an input layer and previous layers, and reserves high-resolution image contour information, the object contour map has a higher resolution and is clearer, and is combined with the medical image to obtain a clear and visualized classification result interpretation diagram.

In certain embodiments, a branch based on a feature map inputted by a last layer of convolution is further provided in addition to the branch of the foregoing backpropagation algorithm. Therefore, after the medical image is obtained, a feature map corresponding to the medical image may be further obtained by using a medical image classification model, the feature map including N channels, N being an integer greater than 1. A thermodynamic diagram corresponding to the medical image content recognition result is generated according to the feature map and a weight parameter set, the weight parameter set including N weight parameters, the weight parameters having a correspondence with the channels. Correspondingly, in A5, a manner of generating an image recognition result corresponding to the medical image according to the object contour map may be generating the image recognition result corresponding to the medical image according to the thermodynamic diagram and the object contour map.

Implementations of the steps in this embodiment may be similar to those in the foregoing embodiments, and details are not described herein again.

Figure 11B:
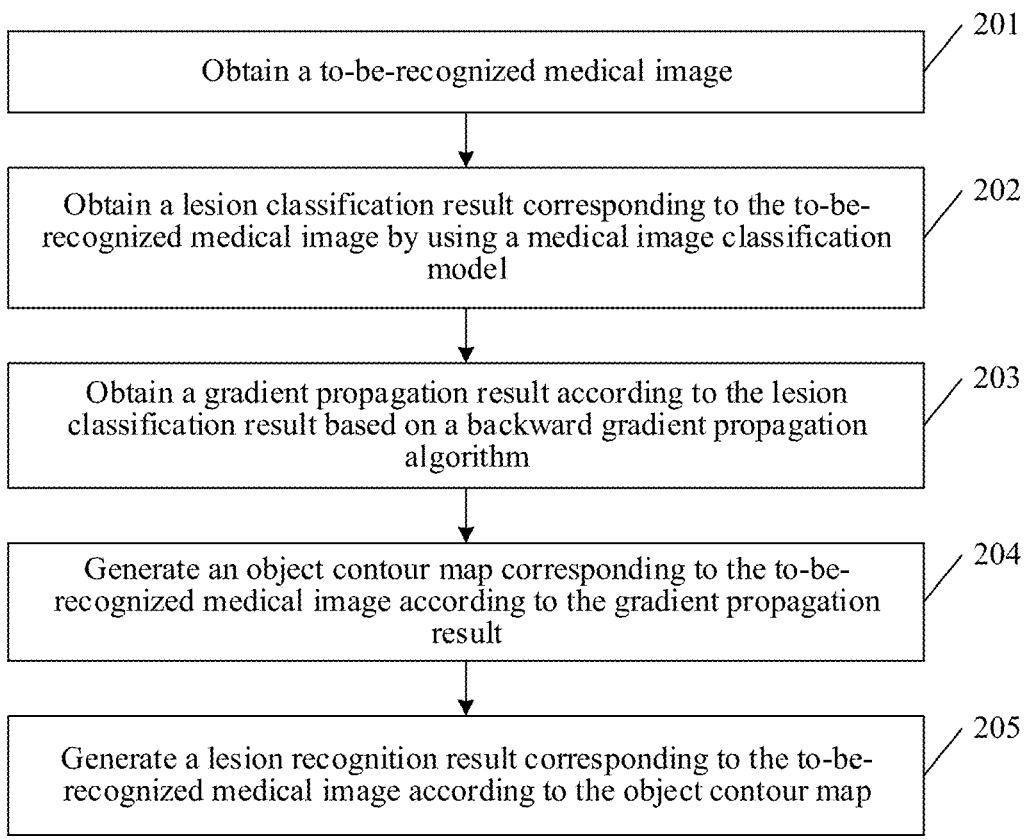
FIG. 11B is a schematic diagram of another embodiment of a medical image recognition method according to one or more embodiments of the present disclosure.

With reference to the foregoing description, the medical image recognition method in the present disclosure is described below. Referring to FIG. 11B, an embodiment of the medical image recognition method in the embodiments of the present disclosure includes the following steps:

201. Obtain a medical image.

In this embodiment, the image recognition apparatus obtains the medical image. The image recognition apparatus may be deployed on a terminal device, a server, or a medical device, which is not limited herein. The medical image is specifically an endoscopic image. The endoscopic images involved in the present disclosure include, but not limited to, an endoscopic image of a gastrointestinal tract, an endoscopic image of a pancreas, an endoscopic image of a biliary tract, an endoscopic image of a respiratory tract, and an endoscopic image of a urinary tract.

202. Obtain a lesion classification result corresponding to the medical image by using a medical image classification model.

In this embodiment, the image recognition apparatus inputs the medical image to the medical image classification model, and the medical image classification model outputs the lesion classification result corresponding to the medical image. In addition, in the process of outputting the lesion classification result, the feature map may be outputted after the medical image passes through a plurality of cascaded convolutional layers. In certain embodiments, the medical image classification model is a neural network based on deep convolution, such as a VGG network, a res-net or a dense-net, and a main body of the medical image classification model is formed by stacking convolutional layers.

A feature map outputted through a last convolutional layer is obtained after the medical image passes through a plurality of cascaded convolutional layers and pooling layers. The feature map then passes through the GAP layer, that is, an average value of a feature map of each channel is obtained, to obtain a vector (a size of which is 1*N). Then, the vector is mapped to a prediction score of each class (a size of which is 1×C, where C is a quantity of classes) through a fully-connected layer. A class with a highest score is obtained from all classes as the lesion classification result of the medical image.

Classes of a small intestine are used as an example. The classes include, but not limited to, a small intestine tumor, a smooth muscle tumor, a sarcoma, a polyp, a lymphoma, and an inflammation.

203. Obtain a gradient propagation result according to the lesion classification result based on a backward gradient propagation algorithm.

In this embodiment, the image recognition apparatus obtains the gradient propagation result according to the lesion classification result by using a backward gradient propagation algorithm. Specifically, the backward gradient propagation algorithm herein may be a guided backpropagation algorithm.

204. Generate an object contour map corresponding to the medical image according to the gradient propagation result.

In this embodiment, the image recognition apparatus generates the object contour map corresponding to the medical image by using the gradient propagation result. In certain embodiments, for a manner of generating, by the image recognition apparatus, the object contour map, reference may be made to the foregoing embodiments. Details are not described herein again.

205. Generate a lesion recognition result corresponding to the medical image according to the object contour map.

In this embodiment, the image recognition apparatus superimposes the object contour map generated at step 204 on the original image (that is, the medical image) to generate a classification result interpretation diagram. In certain embodiments, the lesion recognition result may include only the classification result interpretation diagram, or include both the classification result interpretation diagram and information related to a lesion classification result such as a name of the lesion classification result, a development situation of a lesion, and related data of a patient.

In this embodiment of the present disclosure, a medical image recognition method is provided. A medical image is first obtained, a lesion classification result corresponding to the medical image is then obtained by using a medical image classification model, an object contour map is obtained according to the lesion classification result based on a backward gradient propagation algorithm, and a lesion recognition result corresponding to the medical image is finally generated according to the object contour map. In the foregoing manner, a lesion classification result based on the medical image is obtained, and an object contour map may be further obtained. The object contour map gains a contour feature of all objects in an overall image. Because the object contour map adopts convolutional network results of an input layer and previous layers, and reserves high-resolution image contour information, the object contour map has a higher resolution and is clearer, and is combined with the medical image to obtain a clear and visualized classification result interpretation diagram.

In certain embodiments, based on the embodiment corresponding to FIG. 11B, the method may further include: processing the medical image by using a convolutional layer of the medical image classification model, to obtain a feature map corresponding to the medical image, the feature map including N channels, N being an integer greater than 1; and generating a thermodynamic diagram corresponding to the lesion classification result according to the feature map and a weight parameter set, the weight parameter set including N weight parameters, the weight parameters having a correspondence with the channels; and the generating a lesion recognition result corresponding to the medical image according to the object contour map may include: generating a lesion recognition result corresponding to the medical image according to the thermodynamic diagram and the object contour map.

In this embodiment, a method for generating a lesion recognition result based on the thermodynamic diagram and the object contour map is described. In a manner of step 201 to step 205, the object contour map corresponding to the medical image may be predicted. The object contour map can well reserve high-resolution image contour information, but has no relationship with a specified class. To well distinguish different classes of discriminative regions, another branch is introduced to the present disclosure. That is, a thermodynamic diagram corresponding to the lesion classification result is generated according to the feature map and the weight parameter set.

It is assumed that the inputted medical image is an RGB image, and a size of the medical image is expressed as H*W*3. A feature map outputted through a last convolutional layer is obtained after the medical image passes through a plurality of cascaded convolutional layers and pooling layers. The feature map is represented by $F_n(x,y)$, and n in the feature map $F_n(x,y)$ represents a feature map of an nth channel. That is, n=0, 1, 2, . . . , or N−1, and a size of the feature map is expressed as X*Y*N. (x,y) represents a spatial position in the feature map. That is, x=0, 1, 2, . . . or X−1, and y=0, 1, 2, . . . , or Y−1.

The image recognition apparatus generates the thermodynamic diagram corresponding to the lesion classification result according to the feature map and the weight parameter set, the weight parameter set including N weight parameters. That is, each channel of the feature map corresponds to one weight parameter. The weight parameter may be preset according to an empirical value or obtained through training. This is not limited herein. For each of the C classes, one thermodynamic diagram may be obtained. In certain embodiments, for a procedure of generating the thermodynamic diagram, reference may be made to FIG. 4 and related descriptions corresponding to FIG. 4. Details are not described herein again. In actual implementation, upsampling further may need to be performed on the thermodynamic diagram, and a size the same as that of the original image (that is, the medical image) is then obtained, to superimpose the thermodynamic diagram on the original image (that is, the medical image) for presentation. The image recognition apparatus combines the thermodynamic diagram with the object contour map, to generate a lesion recognition result corresponding to the medical image. Specifically, a classification result interpretation diagram may be obtained by multiplying pixels of the object contour map by pixels of the thermodynamic diagram point by point, and the lesion recognition result is generated based on the classification result interpretation diagram. Therefore, high-level semantic information (that is, the thermodynamic diagram) is combined with low-level semantic information (that is, the object contour map).

Further, in this embodiment of the present disclosure, a method for generating a lesion recognition result based on the thermodynamic diagram and the object contour map is provided. That is, a medical image is processed by using a convolutional layer of a medical image classification model, to obtain a feature map corresponding to the medical image, a thermodynamic diagram corresponding to a lesion recognition result is then generated according to the feature map and a weight parameter set, and the lesion recognition result corresponding to the medical image is finally generated according to the thermodynamic diagram and the object contour map. By using the foregoing manner, a discriminative region corresponding to the lesion classification result may be further visualized by using the thermodynamic diagram while the lesion classification result based on the medical image is obtained. This not only provides good interpretability for the model, but also provides a powerful basis for automatic diagnosis, so that the model is more convincing. A doctor and a patient can obtain a clear and visualized classification result interpretation diagram by combining the object contour map with the thermodynamic diagram, which is conducive to more accurate diagnosis of the endoscopic image, thereby improving the reliability of diagnosis based on the medical image.

Figure 12:
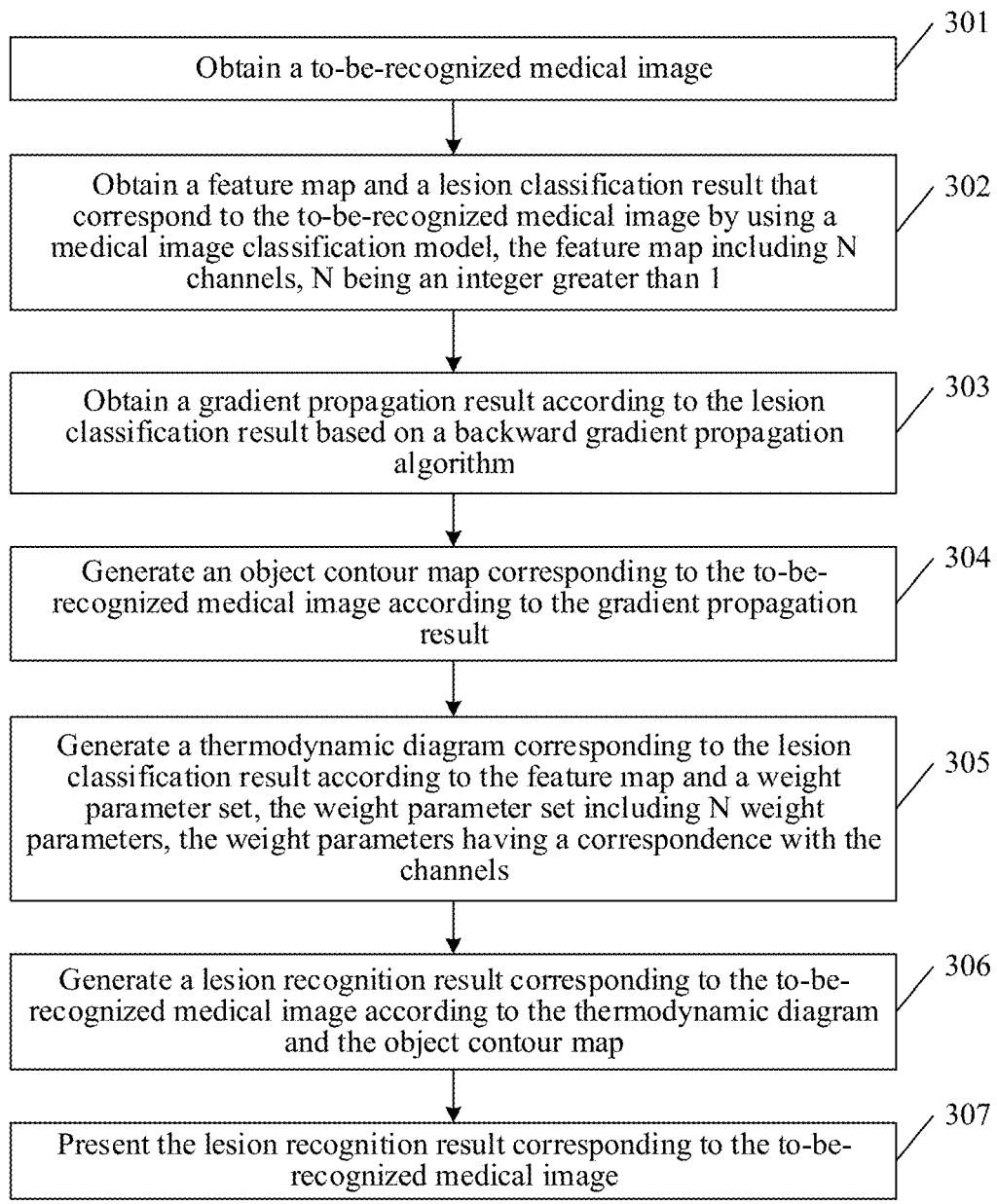
FIG. 12 is a schematic diagram of an embodiment of an image recognition result presentation method according to one or more embodiments of the present disclosure.

Possible implementations of the steps in this embodiment may be similar to those in the foregoing embodiments, and details are not described herein again. With reference to the foregoing description, the image recognition result presentation method in the present disclosure is described below. Referring to FIG. 12, an embodiment of the image recognition result presentation method in the embodiments of the present disclosure includes the following steps:

301. Obtain a medical image.

In this embodiment, the image recognition result presentation apparatus obtains the medical image. The image recognition result presentation apparatus may be deployed on a terminal device or a medical device, which is not limited herein. The medical image is specifically an endoscopic image. The endoscopic images involved in the present disclosure include, but not limited to, an endoscopic image of a gastrointestinal tract, an endoscopic image of a pancreas, an endoscopic image of a biliary tract, an endoscopic image of a respiratory tract, and an endoscopic image of a urinary tract.

302. Obtain a feature map and a lesion classification result that correspond to the medical image by using a medical image classification model, the feature map including N channels, N being an integer greater than 1.

The image recognition result presentation apparatus inputs the medical image to the medical image classification model, and the medical image classification model outputs the lesion classification result corresponding to the medical image. In addition, in the process of outputting the lesion classification result, the feature map may be outputted after the medical image passes through a plurality of cascaded convolutional layers. In certain embodiments, the medical image classification model is a neural network based on deep convolution and a main body of the medical image classification model is formed by stacking convolutional layers.

It is assumed that the inputted medical image is an RGB image, and a size of the medical image is expressed as H*W*3. A feature map outputted through a last convolutional layer is obtained after the medical image passes through a plurality of cascaded convolutional layers and pooling layers. The feature map is represented by $F_n(x,y)$, and n in the feature map $F_n(x,y)$ represents a feature map of an nth channel. That is, n=0, 1, 2, ..., or N−1, and a size of the feature map is expressed as X*Y*N. (x,y) represents a spatial position in the feature map. That is, x=0, 1, 2, ... or X−1, and y=0, 1, 2, ..., or Y−1.

The feature map passes through the GAP layer, that is, an average value of a feature map of each channel is obtained, to obtain a vector (a size of which is 1*N). Then, the vector is mapped to a prediction score of each class (a size of which is 1×C, where C is a quantity of classes) through a fully-connected layer. A class with a highest score is obtained from all classes as the lesion classification result of the medical image.

Classes of a small intestine are used as an example. The classes include, but not limited to, a small intestine tumor, a smooth muscle tumor, a sarcoma, a polyp, a lymphoma, and an inflammation.

303. Obtain a gradient propagation result according to the lesion classification result based on a backward gradient propagation algorithm.

In this embodiment, the image recognition result presentation apparatus obtains the gradient propagation result according to the lesion classification result by using the backward gradient propagation algorithm. The backward gradient propagation algorithm herein may be a guided backpropagation algorithm.

304. Generate an object contour map corresponding to the medical image according to the gradient propagation result.

In this embodiment, the image recognition result presentation apparatus generates the object contour map corresponding to the medical image by using the gradient propagation result. In certain embodiments, for a manner of generating, by the image recognition result presentation apparatus, the object contour map, reference may be made to the foregoing embodiments. Details are not described herein again.

305. Generate a thermodynamic diagram corresponding to the lesion classification result according to the feature map and a weight parameter set, the weight parameter set including N weight parameters, the weight parameters having a correspondence with the channels.

In this embodiment, the image recognition result presentation apparatus generates the thermodynamic diagram corresponding to the lesion classification result according to the feature map and the weight parameter set, the weight parameter set including N weight parameters. That is, each channel of the feature map corresponds to one weight parameter. The weight parameter may be preset according to an empirical value or obtained through training. This is not limited herein.

For each of the C classes, one thermodynamic diagram may be obtained. In certain embodiments, for a procedure of generating the thermodynamic diagram, reference may be made to FIG. 4 and related descriptions corresponding to FIG. 4. Details are not described herein again. In actual implementation, upsampling further may need to be performed on the thermodynamic diagram, and a size the same as that of the original image (that is, the medical image) is then obtained, to superimpose the thermodynamic diagram on the original image (that is, the medical image) for presentation.

306. Generate a lesion recognition result corresponding to the medical image according to the thermodynamic diagram and the object contour map.

In this embodiment, the image recognition result presentation apparatus may obtain a classification result interpretation diagram by multiplying pixels of the object contour map by pixels of the thermodynamic diagram point by point, and generate the lesion recognition result based on the classification result interpretation diagram. Therefore, high-level semantic information (that is, the thermodynamic diagram) is combined with low-level semantic information (that is, the object contour map).

307. Present the lesion recognition result corresponding to the medical image.

In this embodiment, the image recognition result presentation apparatus presents the lesion recognition result corresponding to the medical image. In certain embodiments, the lesion recognition result may include only the classification result interpretation diagram, or include both the classification result interpretation diagram and information related to a lesion classification result such as a name of the lesion classification result, a development situation of a lesion, and related data of a patient.

Figure 13:
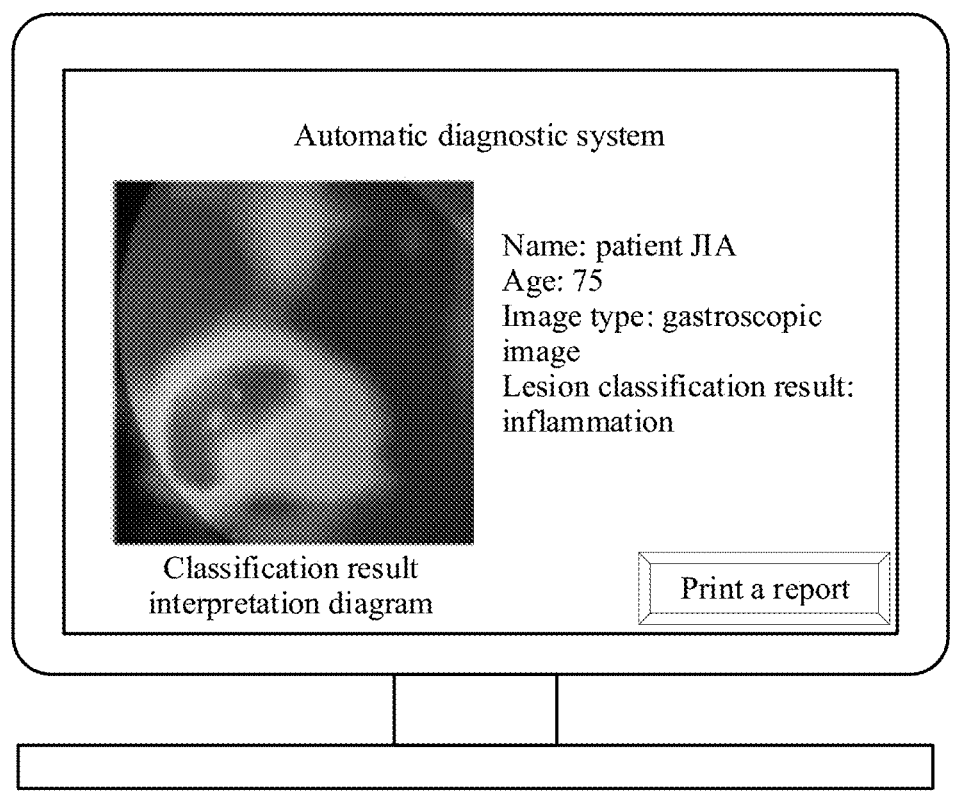
FIG. 13 is a schematic diagram of an interface of presenting a lesion recognition result according to one or more embodiments of the present disclosure.

FIG. 13 is a schematic diagram of an interface of presenting a lesion recognition result according to an embodiment of the present disclosure. As shown in the figure, a classification result interpretation diagram is presented on an interface of a medical imaging system, and other related information may be further presented on the interface. For example, a name of a patient is "JIA", an age of the patient is "75", the classification result interpretation diagram is obtained by analyzing a gastroscopic image, and a lesion classification result is "inflammation". If a doctor may need to print the information on the interface, the doctor may trigger a "print a report" module on the interface to generate a paper report.

In this embodiment of the present disclosure, an image recognition result presentation method is provided. In the foregoing manner, while a lesion classification result based on a medical image is obtained, not only a discriminative region corresponding to the lesion classification result may be visualized by using a thermodynamic diagram, but also an object contour map may be obtained. The object contour map gains a contour feature of all objects in an overall image. Because the object contour map adopts convolutional network results of an input layer and previous layers, and reserves high-resolution image contour information, the object contour map has a higher resolution and is clearer, and is combined with the thermodynamic diagram to obtain a clear and visualized classification result interpretation diagram, which is conducive to more accurate diagnosis of the endoscopic image, thereby improving the reliability of diagnosis based on the medical image.

Figure 14A:
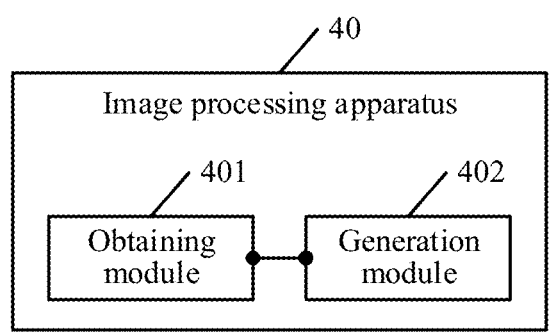
FIG. 14A is a schematic diagram of an embodiment of an image processing apparatus according to one or more embodiments of the present disclosure.

An image recognition apparatus in the present disclosure is described below in detail. FIG. 14A is a schematic diagram of an embodiment of an image processing apparatus according to an embodiment of the present disclosure. The image processing apparatus 40 includes: an obtaining module 401, configured to obtain a medical image, the obtaining module 401 being further configured to obtain a feature map and a medical image content recognition result that correspond to the medical image by using a medical image classification model, the feature map including N channels, N being an integer greater than 1; and a generation module 402, configured to generate a thermodynamic diagram corresponding to the medical image content recognition result according to the feature map and a weight parameter set, the weight parameter set including N weight parameters, the weight parameters having a correspondence with the channels; and the generation module 402 being further configured to generate an image recognition result corresponding to the medical image according to the thermodynamic diagram.

In certain embodiments, based on the embodiment corresponding to FIG. 14A, in another embodiment of the image processing apparatus 40 provided in the embodiments of the present disclosure, the obtaining module 401 is further configured to obtain a feature map and a medical image content recognition result that correspond to the medical image by using a medical image classification model, and then obtain a gradient propagation result according to the medical image content recognition result based on a backward gradient propagation algorithm; the generation module 402 is further configured to generate an object contour map corresponding to the medical image according to the gradient propagation result; and the generation module 402 is further configured to generate the image recognition result corresponding to the medical image according to the thermodynamic diagram and the object contour map.

In certain embodiments, based on the embodiment corresponding to FIG. 14A, in another embodiment of the image processing apparatus 40 provided in the embodiments of the present disclosure, the obtaining module 401 is configured to obtain the feature map corresponding to the medical image by using a convolutional layer of the medical image classification model; process the feature map by using a global average pooling (GAP) layer of the medical image classification model, to obtain a feature vector; calculate C class prediction scores according to the feature vector and the weight parameter set, each class prediction score being corresponding to one class, C being an integer greater than or equal to 1; and determine the medical image content recognition result from C classes according to the C class prediction scores.

In certain embodiments, based on the embodiment corresponding to FIG. 14A, in another embodiment of the image processing apparatus 40 provided in the embodiments of the present disclosure, the obtaining module 401 is configured to obtain the gradient propagation result according to the medical image content recognition result based on a guided backpropagation algorithm, the guided backpropagation algorithm being used for back passing a feature corresponding to a position in which both a gradient and an input value are greater than 0.

Figure 14B:
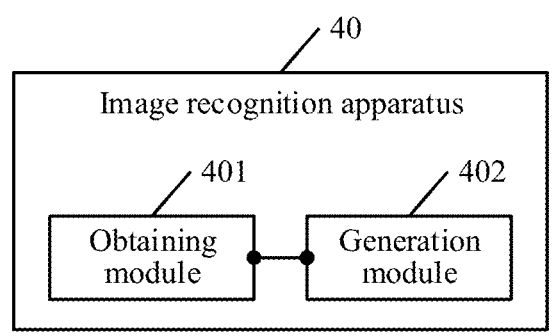
FIG. 14B is a schematic diagram of an embodiment of an image recognition apparatus according to one or more embodiments of the present disclosure.

An image recognition apparatus in the present disclosure is described below in detail. FIG. 14B is a schematic diagram of an embodiment of an image recognition apparatus according to an embodiment of the present disclosure. The image recognition apparatus 40 includes: an obtaining module 401, configured to obtain a medical image, the obtaining module 401 being further configured to obtain a feature map and a lesion classification result that correspond to the medical image by using a medical image classification model, the feature map including N channels, N being an integer greater than 1; and a generation module 402, configured to generate a thermodynamic diagram corresponding to the lesion classification result according to the feature map obtained by the obtaining module 401 and a weight parameter set, the weight parameter set including N weight parameters, the weight parameters having a correspondence with the channels; and the generation module 402 being further configured to generate a lesion recognition result corresponding to the medical image according to the thermodynamic diagram.

In certain embodiments, based on the embodiment corresponding to FIG. 14B, in another embodiment of the image recognition apparatus 40 provided in the embodiments of the present disclosure, the obtaining module 401 is further configured to obtain a feature map and a lesion classification result that correspond to the medical image by using a medical image classification model, and then obtain a gradient propagation result according to the lesion classification result based on a backward gradient propagation algorithm; the generation module 402 is further configured to generate an object contour map corresponding to the medical image according to the gradient propagation result obtained by the obtaining module 401; and the generation module 402 is specifically configured to generate a lesion recognition result corresponding to the medical image according to the thermodynamic diagram and the object contour map.

In certain embodiments, based on the embodiment corresponding to FIG. 14B, in another embodiment of the image recognition apparatus 40 provided in the embodiments of the present disclosure, the obtaining module 401 is specifically configured to: obtain the feature map corresponding to the medical image by using a convolutional layer of the medical image classification model; process the feature map by using a GAP layer of the medical image classification model, to obtain a feature vector; calculate C class prediction scores according to the feature vector and the weight parameter set, each class prediction score being corresponding to one class, C being an integer greater than or equal to 1; and determine the lesion classification result from C classes according to the C class prediction scores.

In certain embodiments, based on the embodiment corresponding to FIG. 14B, in another embodiment of the image recognition apparatus 40 provided in the embodiments of the present disclosure, the obtaining module 401 is specifically configured to calculate the class prediction score in the following manner:

$$Y_c = \sum_n w_n^c \sum_{(x,y)} F_n(x, y),$$

where $Y_c$ represents a class prediction score corresponding to a $c^{th}$ class, C represents a total quantity of classes, $F_n(x,y)$ represents a feature map of an $n^{th}$ channel, $(x,y)$ represents a spatial position in the feature map, and $w_n^c$ represents a weight parameter of the feature map of the $n^{th}$ channel on a prediction being the $c^{th}$ class.

In certain embodiments, based on the embodiment corresponding to FIG. 14B, in another embodiment of the image recognition apparatus 40 provided in the embodiments of the present disclosure, the generation module 402 is specifically configured to generate a thermodynamic diagram in the following manner:

$$P_c(x, y) = \sum_n w_n^c F_n(x, y),$$

where $Y_c$ represents a thermodynamic diagram corresponding to a $c^{th}$ class, the thermodynamic diagram is obtained through upsampling, $F_n(x,y)$ represents a feature map of an $n^{th}$ channel, $(x,y)$ represents a spatial position in the feature map, $w_n^c$ represents a weight parameter of the feature map of the $n^{th}$ channel on a prediction being the $c^{th}$ class, and the $c^{th}$ class belongs to the lesion classification result.

In certain embodiments, based on the embodiment corresponding to FIG. 14B, in another embodiment of the image recognition apparatus 40 provided in the embodiments of the present disclosure, the obtaining module 401 is specifically configured to obtain the gradient propagation result according to the lesion classification result based on a guided backpropagation algorithm, the guided backpropagation algorithm being used for back passing a feature corresponding to a position in which both a gradient and an input value are greater than 0.

In certain embodiments, based on the embodiment corresponding to FIG. 14B, in another embodiment of the image recognition apparatus 40 provided in the embodiments of the present disclosure, the generation module 402 is specifically configured to generate the lesion recognition result by using the following method: $Visual_c(x,y)=G_c(x,y) \odot P_c(x,y)$, $(x,y)$, where $Visual_c(x,y)$ represents a lesion recognition result corresponding to a $c^{th}$ class $G_c(x,y)$ represents an object contour map corresponding to the $c^{th}$ class, $P_c(x,y)$, represents a thermodynamic diagram corresponding to the $c^{th}$ class, the thermodynamic diagram is obtained through upsampling, and the $c^{th}$ class belongs to the lesion classification result.

Figure 15:
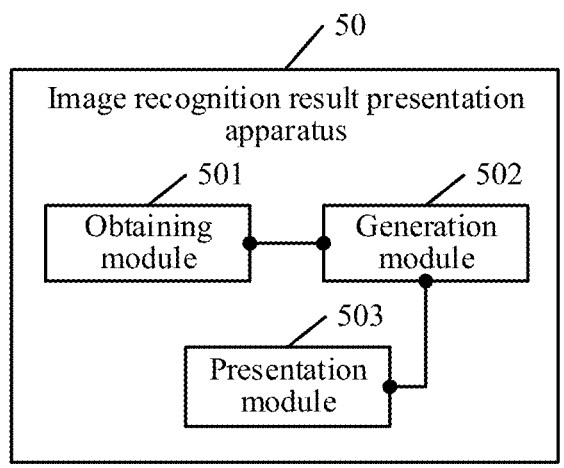
FIG. 15 is a schematic diagram of an embodiment of an image recognition result presentation apparatus according to one or more embodiments of the present disclosure.

An image recognition result presentation apparatus in the present disclosure is described below in detail. FIG. 15 is a schematic diagram of an embodiment of an image recognition result presentation apparatus according to an embodiment of the present disclosure. The image recognition result presentation apparatus 50 includes: an obtaining module 501, configured to obtain a medical image, the obtaining module 501 being further configured to obtain a feature map and a lesion classification result that correspond to the medical image by using a medical image classification model, the feature map including N channels, N being an integer greater than 1; and the obtaining module 501 being further configured to obtain a gradient propagation result according to the lesion classification result based on a backward gradient propagation algorithm; a generation module 502, configured to generate an object contour map corresponding to the medical image according to the gradient propagation result obtained by the obtaining module 501, the generation module 502 being further configured to generate a thermodynamic diagram corresponding to the lesion classification result according to the feature map and a weight parameter set, the weight parameter set including N weight parameters, the weight parameters having a correspondence with the channels; and the generation module 502 being further configured to generate a lesion recognition result corresponding to the medical image according to the thermodynamic diagram and the object contour map; and a presentation module 503, configured to present the lesion recognition result that corresponds to the medical image and is generated by the generation module 502.

Figure 16A:
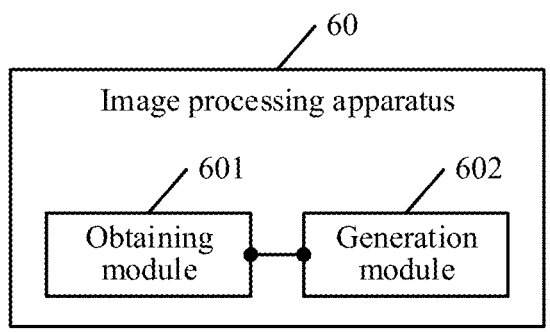
FIG. 16A is a schematic diagram of an embodiment of an image processing apparatus according to one or more embodiments of the present disclosure.

An image processing apparatus in the present disclosure is described below in detail. FIG. 16A is a schematic diagram of an embodiment of an image processing apparatus according to an embodiment of the present disclosure. The image processing apparatus 60 includes: an obtaining module 601, configured to obtain a medical image, the obtaining module 601 being further configured to obtain a medical image content recognition result corresponding to the medical image by using a medical image classification model; and the obtaining module 601 being further configured to obtain a gradient propagation result according to the medical image content recognition result based on a backward gradient propagation algorithm; and a generation module 602, configured to generate an object contour map corresponding to the medical image according to the gradient propagation result obtained by the obtaining module, the generation module 602 being further configured to generate the image recognition result corresponding to the medical image according to the object contour map.

In certain embodiments, based on the embodiment corresponding to FIG. 16A, in another embodiment of the image processing apparatus 60 provided in the embodiments of the present disclosure, the obtaining module 601 is further configured to obtain a medical image, and then obtain the feature map corresponding to the medical image by using the medical image classification model, the feature map being obtained by convoluting the medical image by using a convolutional layer of the medical image classification model, the feature map including N channels, N being an integer greater than 1; the generation module 602 is further configured to generate a thermodynamic diagram corresponding to the medical image content recognition result according to the feature map and a weight parameter set, the weight parameter set including N weight parameters, the weight parameters having a correspondence with the channels; and the generation module 602 is further configured to generate the image recognition result corresponding to the medical image according to the thermodynamic diagram and the object contour map.

Figure 16B:
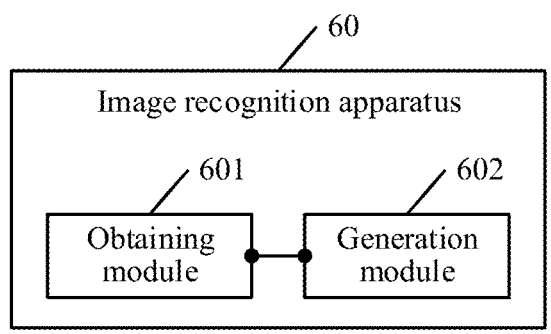
FIG. 16B is a schematic diagram of an embodiment of an image recognition apparatus according to one or more embodiments of the present disclosure.

An image recognition apparatus in the present disclosure is described below in detail. FIG. 16B is a schematic diagram of an embodiment of an image recognition apparatus according to an embodiment of the present disclosure. The image recognition apparatus 60 includes: an obtaining module 601, configured to obtain a medical image, the obtaining module 601 being further configured to obtain a lesion classification result corresponding to the medical image by using a medical image classification model; and the obtaining module 601 being further configured to obtain a gradient propagation result according to the lesion classification result based on a backward gradient propagation algorithm; a generation module 602, configured to generate an object contour map corresponding to the medical image according to the gradient propagation result obtained by the obtaining module 601, the generation module 602 being further configured to generate a lesion recognition result corresponding to the medical image according to the object contour map.

Figure 17:
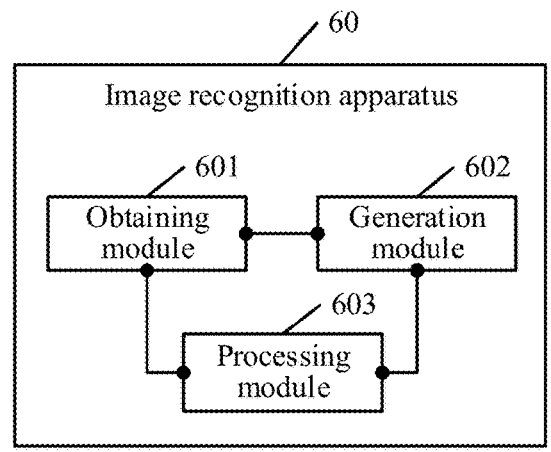
FIG. 17 is a schematic diagram of another embodiment of an image recognition apparatus according to one or more embodiments of the present disclosure.

In certain embodiments, based on the embodiment corresponding to FIG. 16B, referring to FIG. 17, in another embodiment of the image recognition apparatus 60 provided in the embodiments of the present disclosure, the image recognition apparatus 60 further includes a processing module 603, where the processing module 603 is configured to process the medical image by using a convolutional layer of the medical image classification model, to obtain a feature map corresponding to the medical image, the feature map including N channels, N being an integer greater than 1; the generation module 602 is further configured to generate a thermodynamic diagram corresponding to the lesion classification result according to the feature map obtained through processing by the processing module 603 and a weight parameter set, the weight parameter set including N weight parameters, the weight parameters having a correspondence with the channels; and the generation module 602 is specifically configured to generate a lesion recognition result corresponding to the medical image according to the thermodynamic diagram and the object contour map.

In certain embodiments, based on the embodiment corresponding to FIG. 16B or FIG. 17, in another embodiment of the image recognition apparatus 60 provided in the embodiments of the present disclosure, the obtaining module 601 is specifically configured to: process the feature map by using a GAP layer of the medical image classification model, to obtain a feature vector; calculate C class prediction scores according to the feature vector and the weight parameter set, each class prediction score being corresponding to one class, C being an integer greater than or equal to 1; and determine the lesion classification result from C classes according to the C class prediction scores.

In certain embodiments, based on the embodiment corresponding to FIG. 16B or FIG. 17, in another embodiment of the image recognition apparatus 60 provided in the embodiments of the present disclosure, the obtaining module 601 is specifically configured to calculate the class prediction score in the following manner:

$$Y_c = \sum_n w_n^c \sum_{(x,y)} F_n(x, y),$$

where $Y_c$ represents a class prediction score corresponding to a $c^{th}$ class, C represents a total quantity of classes, $F_n(x,y)$ represents a feature map of an $n^{th}$ channel, $(x,y)$ represents a spatial position in the feature map, and represents a weight parameter of the feature map of the $n^{th}$ channel on a prediction being the $c^{th}$ class.

In certain embodiments, based on the embodiment corresponding to FIG. 16B or FIG. 17, in another embodiment of the image recognition apparatus 60 provided in the embodiments of the present disclosure, the generation module 602 is specifically configured to generate a thermodynamic diagram in the following manner:

$$P_c(x, y) = \sum_n w_n^c F_n(x, y),$$

where $P_c(x,y)$ represents a thermodynamic diagram corresponding to a $c^{th}$ class, the thermodynamic diagram is obtained through upsampling, $F_n(x,y)$ represents a feature map of an $n^{th}$ channel, $(x,y)$ represents a spatial position in the feature map, $w_n^c$ represents a weight parameter of the feature map of the $n^{th}$ channel on a prediction being the $c^{th}$ class, and the $c^{th}$ class belongs to the lesion classification result.

In certain embodiments, based on the embodiment corresponding to FIG. 16B or FIG. 17, in another embodiment of the image recognition apparatus 60 provided in the embodiments of the present disclosure, the obtaining module 601 is specifically configured to obtain the gradient propagation result according to the lesion classification result based on a guided backpropagation algorithm, the guided backpropagation algorithm being used for back passing a feature corresponding to a position in which both a gradient and an input value are greater than 0.

In certain embodiments, based on the embodiment corresponding to FIG. 16B or FIG. 17, in another embodiment of the image recognition apparatus 60 provided in the embodiments of the present disclosure, the generation module 602 is specifically configured to generate the lesion recognition result by using the following method: $Visual_c(x,y)=G_c(x,y)\odot P_c(x,y)$, where $Visual_c(x,y)$, where $Visual_c(x,y)$ represents a lesion recognition result corresponding to a $c^{th}$ class, $G_c(x,y)$ represents an object contour map corresponding to the $c^{th}$ class, $P_c(x,y)$ represents a thermodynamic diagram corresponding to the $c^{th}$ class, the thermodynamic diagram is obtained through upsampling, and the $c^{th}$ class belongs to the lesion classification result.

Figure 18:
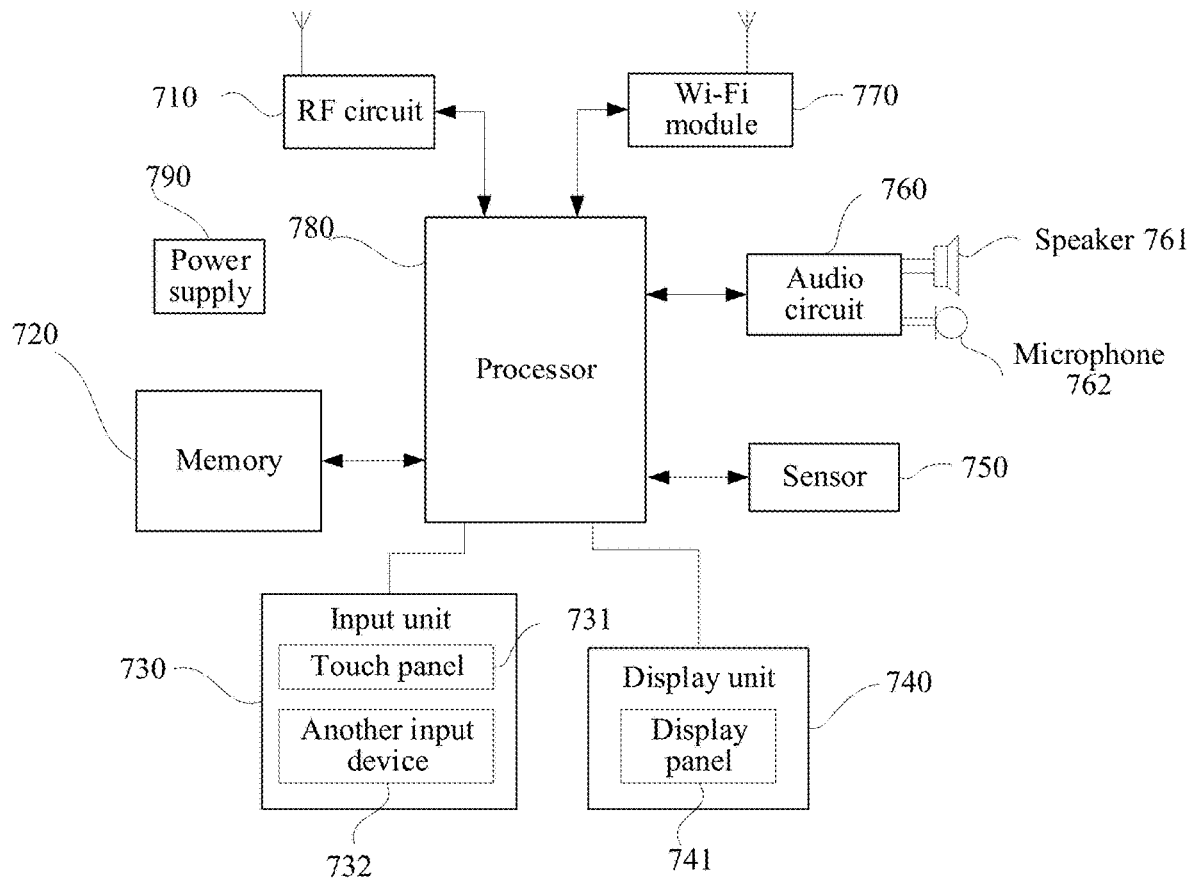
FIG. 18 is a schematic structural diagram of a terminal device according to one or more embodiments of the present disclosure.

The embodiments of the present disclosure further provide another image recognition apparatus and image recognition result presentation apparatus. As shown in FIG. 18, for ease of description, only parts related to the embodiments of the present disclosure are shown. For specific technical details that are not disclosed, reference is made to the method part of the embodiments of the present disclosure. That the terminal device is a mobile phone is used as an example:

FIG. 18 is a block diagram of a structure of a part of a mobile phone related to a terminal device according to an embodiment of the present disclosure. Referring to FIG. 18, the mobile phone includes components such as a radio frequency (RF) circuit 710, a memory 720, an input unit 730, a display unit 740, a sensor 750, an audio circuit 760, a wireless fidelity (Wi-Fi) module 770, a processor 780, and a power supply 790. Persons skilled in the art may understand that the structure of the mobile phone shown in FIG. 18 does not constitute a limitation on the mobile phone, and the mobile phone may include more or fewer components than those shown in the figure, or some components may be combined, or a different component deployment may be used. The following describes the components of the mobile phone with reference to FIG. 18 in detail.

The memory 720 may be configured to store a software program and a module. The processor 780 runs the software program and the module that are stored in the memory 720, to perform various functional implementations and data processing of the mobile phone. The memory 720 may include a program storage area and a data storage area. The program storage area may store an operating system, an application program required by at least one function (such as a sound playback function and an image display function), and the like. The data storage area may store data (such as audio data and an address book) created according to the use of the mobile phone, and the like. In addition, the memory 720 may include a high-speed random access memory, and may also include a nonvolatile memory, for example, at least one magnetic disk storage device, a flash memory, or another volatile solid-state storage device.

The processor 780 is the control center of the mobile phone, and is connected to various parts of the entire mobile phone by using various interfaces and lines. By running or executing the software program and/or the module stored in the memory 720, and invoking data stored in the memory 720, the processor performs various functions and data processing of the mobile phone, thereby performing overall monitoring on the mobile phone. In certain embodiments, the processor 780 may include one or more processing units. In certain embodiments, the processor 780 may integrate an application processor and a modem processor, where the application processor processes an operating system, a user interface, an application program, and the like, and the modem processor processes wireless communication. In certain embodiments, the modem may either not be integrated into the processor 780.

In this embodiment of the present disclosure, the processor 780 included in the terminal device further has the following functions: obtaining a medical image; obtaining a feature map and a medical image content recognition result that correspond to the medical image by using a medical image classification model, the feature map including N channels, N being an integer greater than 1; generating a thermodynamic diagram corresponding to the medical image content recognition result according to the feature map and a weight parameter set, the weight parameter set including N weight parameters, the weight parameters having a correspondence with the channels; and generating an image recognition result corresponding to the medical image according to the thermodynamic diagram.

In this embodiment of the present disclosure, the processor 780 included in the terminal device further has the following functions: obtaining a medical image; obtaining a feature map and a lesion classification result that correspond to the medical image by using a medical image classification model, the feature map including N channels, N being an integer greater than 1; generating a thermodynamic diagram corresponding to the lesion classification result according to the feature map and a weight parameter set, the weight parameter set including N weight parameters, the weight parameters having a correspondence with the channels; and generating a lesion recognition result corresponding to the medical image according to the thermodynamic diagram.

In this embodiment of the present disclosure, the processor 780 included in the terminal device further has the following functions: obtaining a medical image; obtaining a feature map and a lesion classification result that correspond to the medical image by using a medical image classification model, the feature map including N channels, N being an integer greater than 1; obtaining a gradient propagation result according to the lesion classification result based on a backward gradient propagation algorithm; generating an object contour map corresponding to the medical image according to the gradient propagation result; and generating a thermodynamic diagram corresponding to the lesion classification result according to the feature map and a weight parameter set, the weight parameter set including N weight parameters, the weight parameters having a correspondence with the channels; and generating a lesion recognition result corresponding to the medical image according to the thermodynamic diagram and the object contour map; and presenting the lesion recognition result corresponding to the medical image.

In this embodiment of the present disclosure, the processor 780 included in the terminal device further has the following functions: obtaining a medical image; obtaining a medical image content recognition result corresponding to the medical image by using a medical image classification model; obtaining a gradient propagation result according to the medical image content recognition result based on a backward gradient propagation algorithm; generating an object contour map corresponding to the medical image according to the gradient propagation result; and generating an image recognition result corresponding to the medical image according to the object contour map.

In this embodiment of the present disclosure, the processor 780 included in the terminal device further has the following functions: obtaining a medical image; obtaining a lesion classification result corresponding to the medical image by using a medical image classification model; obtaining a gradient propagation result according to the lesion classification result based on a backward gradient propagation algorithm; generating an object contour map corresponding to the medical image according to the gradient propagation result; and generating a lesion recognition result corresponding to the medical image according to the object contour map.

Figure 19:
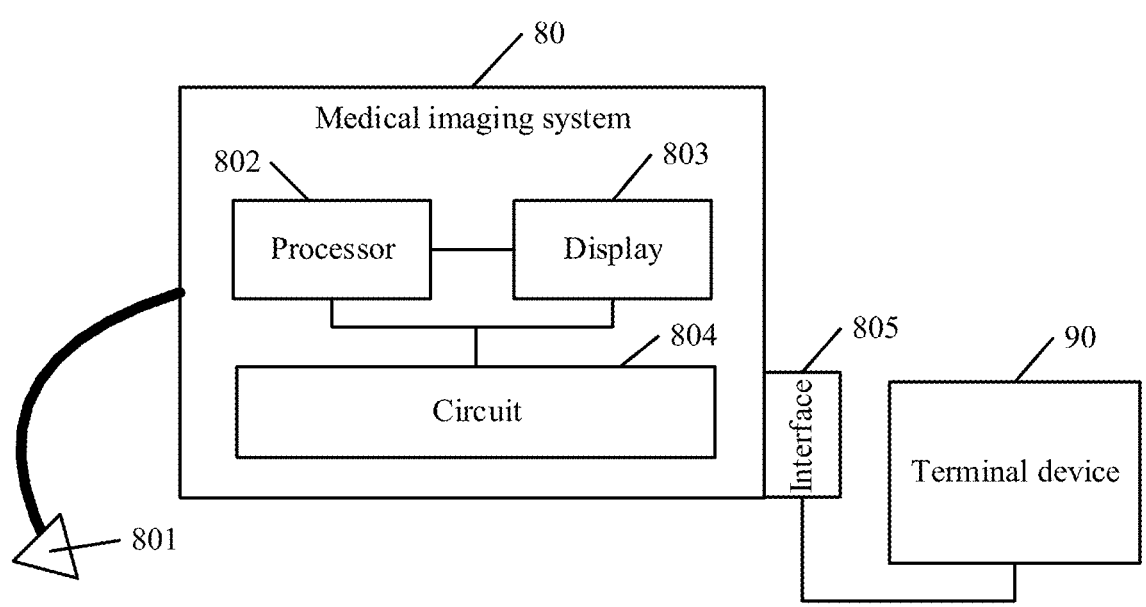
FIG. 19 is a schematic structural diagram of a medical imaging system according to one or more embodiments of the present disclosure.

FIG. 19 is a structural diagram of a medical imaging system 80 according to an implementation of the present disclosure. The medical imaging system 80 in this implementation is a system for supporting an endoscopy service. The medical imaging system 80 includes a probe 801, a processor 802, a display 803, a circuit 804, and an interface 805. The medical imaging system 80 can work together with a terminal device 90. The probe 801 may be specifically an endoscopic probe, which may be inserted into an esophagus, a stomach, an intestine, a bronchus, or the like for real-time scanning and imaging. A doctor can clearly identify a growth level and an invasion depth of a tumor by using the endoscopic probe. In addition, the endoscopic probe is further applicable to imaging of a visceral organ near an intestinal tract, and plays a role in the diagnosis of lesions in a pancreas, a bile duct, and a gallbladder.

The processor 802 is configured to recognize the endoscopic image obtained by the probe 801 through photography and generate a recognition result. The display 803 displays a lesion recognition result according to an image signal inputted by the processor 802. The lesion recognition result is specifically an image result, and an image obtained by the probe 801 through photography may be displayed in real time. The circuit 804 is configured to connect modules in the medical imaging system 80 and provide electric signals, to enable the medical imaging system 80 to work normally inside and establish a communication connection to the terminal device 90.

The medical imaging system 80 may directly recognize and process the acquired endoscopic image. Alternatively, the medical imaging system may send the acquired endoscopic image to the terminal device 90 through the interface 805, and the terminal device 90 may recognize and process the endoscopic image. The terminal device 90 may make an electronic medical record or prescription, or directly perform printing based on a lesion recognition result sent by the medical imaging system 80.

In this embodiment of the present disclosure, the processor 802 included in the medical imaging system further has the following functions: obtaining a medical image; obtaining a feature map and a medical image content recognition result that correspond to the medical image by using a medical image classification model, the feature map including N channels, N being an integer greater than 1; generating a thermodynamic diagram corresponding to the medical image content recognition result according to the feature map and a weight parameter set, the weight parameter set including N weight parameters, the weight parameters having a correspondence with the channels; and generating an image recognition result corresponding to the medical image according to the thermodynamic diagram. In this embodiment of the present disclosure, the processor 802 included in the medical imaging system further has the following functions: obtaining a feature map and a lesion classification result that correspond to the medical image by using a medical image classification model, the feature map including N channels, N being an integer greater than 1; generating a thermodynamic diagram corresponding to the lesion classification result according to the feature map and a weight parameter set, the weight parameter set including N weight parameters, the weight parameters having a correspondence with the channels; and generating a lesion recognition result corresponding to the medical image according to the thermodynamic diagram.

In this embodiment of the present disclosure, the processor 802 included in the medical imaging system further has the following functions: obtaining a feature map and a lesion classification result that correspond to the medical image by using a medical image classification model, the feature map including N channels, N being an integer greater than 1; obtaining a gradient propagation result according to the lesion classification result based on a backward gradient propagation algorithm; generating an object contour map corresponding to the medical image according to the gradient propagation result; and generating a thermodynamic diagram corresponding to the lesion classification result according to the feature map and a weight parameter set, the weight parameter set including N weight parameters, the weight parameters having a correspondence with the channels; and generating a lesion recognition result corresponding to the medical image according to the thermodynamic diagram and the object contour map; and presenting the lesion recognition result corresponding to the medical image.

In this embodiment of the present disclosure, the processor 802 included in the medical imaging system further has the following functions: obtaining a medical image; obtaining a medical image content recognition result corresponding to the medical image by using a medical image classification model; obtaining a gradient propagation result according to the medical image content recognition result based on a backward gradient propagation algorithm; generating an object contour map corresponding to the medical image according to the gradient propagation result; and generating an image recognition result corresponding to the medical image according to the object contour map.

In this embodiment of the present disclosure, the processor 802 included in the medical imaging system further has the following functions: obtaining a lesion classification result corresponding to the medical image by using a medical image classification model; obtaining a gradient propagation result according to the lesion classification result based on a backward gradient propagation algorithm; generating an object contour map corresponding to the medical image according to the gradient propagation result; and generating a lesion recognition result corresponding to the medical image according to the object contour map.

Persons skilled in the art can clearly understand that for convenience and conciseness of description, for specific working processes of the foregoing described system, apparatus and unit, reference is made to the corresponding processes in the foregoing method embodiments, and details are not described herein again.

In the several embodiments provided in the present disclosure, the disclosed system, apparatus, and method may be implemented in other manners. For example, the described apparatus embodiment is merely exemplary. For example, the unit division is merely a logical function division and may be other division during actual implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electric, mechanical, or other forms.

The units described as separate parts may or may not be physically separate, and components displayed as units may or may not be physical units, that is, may be in one position, or may be distributed on a plurality of network units. Some or all of the units may be selected according to actual requirements to achieve the objectives of the solutions of the embodiments.

In addition, functional units in the embodiments of the present disclosure may be integrated into one processing unit, or each of the units may exist alone physically, or two or more units may be integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage medium. Based on such an understanding, the technical solutions of the present disclosure essentially, or the part contributing to the related art, all or some of the technical solutions may be implemented in a form of a software product. The computer software product is stored in a storage medium, and includes several instructions for instructing a computer device (which may be a personal computer, a server, a network device, or the like) to perform all or some of the steps of the methods in the embodiments of the present disclosure. The foregoing storage medium includes: any medium that can store program code, such as a USB flash drive, a removable hard disk, a read-only memory (ROM), a random access memory (RAM), a magnetic disk, or an optical disc.

The term unit (and other similar terms such as subunit, module, submodule, etc.) in this disclosure may refer to a software unit, a hardware unit, or a combination thereof. A software unit (e.g., computer program) may be developed using a computer programming language. A hardware unit may be implemented using processing circuitry and/or memory. Each unit can be implemented using one or more processors (or processors and memory). Likewise, a processor (or processors and memory) can be used to implement one or more units. Moreover, each unit can be part of an overall unit that includes the functionalities of the unit.

The foregoing embodiments are merely intended for describing the technical solutions of the present disclosure, but not for limiting the present disclosure. Although the present disclosure is described in detail with reference to the foregoing embodiments, persons of ordinary skill in the art understand that they may still make modifications to the technical solutions described in the foregoing embodiments or make equivalent replacements to some technical features thereof, without departing from the spirit and scope of the technical solutions of the embodiments of the present disclosure.

What is claimed is:

1. A medical image processing method, performed by a data processing device, the method comprising:
   obtaining a medical image;
   obtaining a feature map and a medical image content recognition result that correspond to the medical image by using a medical image classification model, or obtaining the feature map and a lesion classification result that correspond to the medical image by using the medical classification model, the feature map including N channels, N being an integer greater than 1;
   generating a thermodynamic diagram corresponding to the medical image content recognition result or the lesion classification result according to the feature map and a weight parameter set, the weight parameter set including N weight parameters, the weight parameters having a correspondence with the channels;
   obtaining a gradient propagation result according to the medical image content recognition result or the lesion classification result based on a backward gradient propagation algorithm;
   generating an object contour map corresponding to the medical image according to the gradient propagation result and convolutional network results of an input layer and previous layers of the medical image classification model, the object contour map describing overall object contour features of the medical image; and
   generating an image recognition result corresponding to the medical image according to the thermodynamic diagram and the object contour map.

2. The method according to claim 1, wherein obtaining the feature map and the medical image content recognition result comprises:
   obtaining the feature map corresponding to the medical image by using a convolutional layer of the medical image classification model;
   processing the feature map by using a global average pooling (GAP) layer of the medical image classification model, to obtain a feature vector;
   calculating C class prediction scores according to the feature vector and the weight parameter set, each class prediction score being corresponding to one class, C being an integer greater than or equal to 1; and
   determining the medical image content recognition result from C classes according to the C class prediction scores.

3. The method according to claim 2, wherein calculating C class prediction scores according to the feature vector and the weight parameter set comprises:
   calculating the class prediction score according to equation $$Y_c = \sum_n w_n^c \sum_{(x,y)} F_n(x, y),$$

wherein $Y_c$ represents a class prediction score corresponding to a $c^{th}$ class, C represents a total quantity of classes, $F_n(x, y)$ represents a feature map of an $n^{th}$ channel, (x, y) represents a spatial position in the feature map, and $w_n^c$ represents a weight parameter of the feature map of the $n^{th}$ channel on a prediction being the $c^{th}$ class.

4. The method according to claim 1, wherein obtaining the gradient propagation result according to the medical image content recognition result or the lesion classification result comprises:
   obtaining the gradient propagation result according to the medical image content recognition result or the lesion classification result based on a guided backpropagation algorithm, the guided backpropagation algorithm being used for back passing a feature corresponding to a position in which both a gradient and an input value are greater than 0.

5. The method according to claim 1, wherein generating the thermodynamic diagram comprises:
   generating the thermodynamic diagram according to equation $$P_c(x, y) = \sum_n w_n^c F_n(x, y),$$

wherein $P_c(x, y)$ represents a thermodynamic diagram corresponding to a $c^{th}$ class, the thermodynamic diagram is obtained through upsampling, $F_n(x, y)$ represents a feature map of an $n^{th}$ channel, (x, y) represents a spatial position in the feature map, $w_n^c$ represents a weight parameter of the feature map of the $n^{th}$ channel on a prediction being the $c^{th}$ class, and the $c^{th}$ class belongs to the lesion classification result.

6. The method according to claim 5, wherein the lesion recognition result is obtained by using equation $$\text{Visual}_c(x,y) = G_c(x,y) \odot P_c(x,y),$$

wherein $\text{Visual}_c(x, y)$ represents a lesion recognition result corresponding to a $c^{th}$ class, $G_c(x,y)$ represents an object contour map corresponding to the $c^{th}$ class, $P_c(x, y)$ represents a thermodynamic diagram corresponding to the $c^{th}$ class, the thermodynamic diagram is obtained through upsampling, the $c^{th}$ class belongs to the lesion classification result, and $\odot$ represents an XNOR operation.

7. The method according to claim 1, wherein obtaining the gradient propagation result comprises:
   obtaining the gradient propagation result according to the medical image content recognition result or the lesion classification result based on a guided backpropagation algorithm, the guided backpropagation algorithm being used for back passing a feature corresponding to a position in which both a gradient and an input value are greater than 0.

8. The method according to claim 1, wherein generating the image recognition result comprises:
multiplying pixels of the object contour map by pixels of the thermodynamic diagram point by point to obtain a classification result interpretation diagram; and
generating the image recognition result based on the classification result interpretation diagram.

9. The method according to claim 1, wherein the object contour map reserves high-resolution image contour information and has no relationship with a specified class.

10. A medical image processing apparatus, comprising: a memory storing computer program instructions; and a processor coupled to the memory and configured to execute the computer program instructions and perform:
obtaining a medical image;
obtaining a feature map and a medical image content recognition result that correspond to the medical image by using a medical image classification model, or obtaining the feature map and a lesion classification result that correspond to the medical image by using the medical classification model, the feature map including N channels, N being an integer greater than 1;
generating a thermodynamic diagram corresponding to the medical image content recognition result or the lesion classification result according to the feature map and a weight parameter set, the weight parameter set including N weight parameters, the weight parameters having a correspondence with the channels;
obtaining a gradient propagation result according to the medical image content recognition result or the lesion classification result based on a backward gradient propagation algorithm;
generating an object contour map corresponding to the medical image according to the gradient propagation result and convolutional network results of an input layer and previous layers of the medical image classification model, the object contour map describing overall object contour features of the medical image; and
generating an image recognition result corresponding to the medical image according to the thermodynamic diagram and the object contour map.

11. The medical image processing apparatus according to claim 10, wherein obtaining the feature map and the medical image content recognition result comprises:
obtaining the feature map corresponding to the medical image by using a convolutional layer of the medical image classification model;
processing the feature map by using a global average pooling (GAP) layer of the medical image classification model, to obtain a feature vector;
calculating C class prediction scores according to the feature vector and the weight parameter set, each class prediction score being corresponding to one class, C being an integer greater than or equal to 1; and
determining the medical image content recognition result from C classes according to the C class prediction scores.

12. The medical image processing apparatus according to claim 11, wherein calculating C class prediction scores according to the feature vector and the weight parameter set comprises:

calculating the class prediction score according to equation $$Y_c = \sum_n w_n^c \sum_{(x,y)} F_n(x, y),$$

wherein $Y_c$ represents a class prediction score corresponding to a $c^{th}$ class, C represents a total quantity of classes, $F_n(x, y)$ represents a feature map of an $n^{th}$ channel, (x, y) represents a spatial position in the feature map, and $w_n^c$ represents a weight parameter of the feature map of the $n^{th}$ channel on a prediction being the $c^{th}$ class.

13. The medical image processing apparatus according to claim 10, wherein obtaining the gradient propagation result according to the medical image content recognition result or the lesion classification result comprises:
obtaining the gradient propagation result according to the medical image content recognition result or the lesion classification result based on a guided backpropagation algorithm, the guided backpropagation algorithm being used for back passing a feature corresponding to a position in which both a gradient and an input value are greater than 0.

14. The medical image processing apparatus according to claim 10, wherein generating the thermodynamic diagram comprises:
generating the thermodynamic diagram according to equation $$P_c(x, y) = \sum_n w_n^c F_n(x, y),$$

wherein $P_c(x, y)$ represents a thermodynamic diagram corresponding to a $c^{th}$ class, the thermodynamic diagram is obtained through upsampling, $F_n(x, y)$ represents a feature map of an $n^{th}$ channel, (x, y) represents a spatial position in the feature map, $w_n^c$ represents a weight parameter of the feature map of the $n^{th}$ channel on a prediction being the $c^{th}$ class, and the $c^{th}$ class belongs to the lesion classification result.

15. The medical image processing apparatus according to claim 14, wherein the lesion recognition result is obtained by using equation $$\mathrm{Visual}_c(x,y) = G_c(x,y) \odot P_c(x,y),$$

wherein $\mathrm{Visual}_c(x, y)$ represents a lesion recognition result corresponding to a $c^{th}$ class, $G_c(x, y)$ represents an object contour map corresponding to the $c^{th}$ class, $P_c(x, y)$ represents a thermodynamic diagram corresponding to the $c^{th}$ class, the thermodynamic diagram is obtained through upsampling, the $c^{th}$ class belongs to the lesion classification result, and $\odot$ represents an XNOR operation.

16. The medical image processing apparatus according to claim 10, wherein obtaining the gradient propagation result comprises:
obtaining the gradient propagation result according to the medical image content recognition result or the lesion classification result based on a guided backpropagation algorithm, the guided backpropagation algorithm being used for back passing a feature corresponding to a position in which both a gradient and an input value are greater than 0.

17. A non-transitory computer-readable storage medium storing computer program instructions executable by at least one processor to perform:
- obtaining a medical image;
- obtaining a feature map and a medical image content recognition result that correspond to the medical image by using a medical image classification model, or obtaining the feature map and a lesion classification result that correspond to the medical image by using the medical classification model, the feature map including N channels, N being an integer greater than 1;
- generating a thermodynamic diagram corresponding to the medical image content recognition result or the lesion classification result according to the feature map and a weight parameter set, the weight parameter set including N weight parameters, the weight parameters having a correspondence with the channels;
- obtaining a gradient propagation result according to the medical image content recognition result or the lesion classification result based on a backward gradient propagation algorithm;
- generating an object contour map corresponding to the medical image according to the gradient propagation result and convolutional network results of an input layer and previous layers of the medical image classification model, the object contour map describing overall object contour features of the medical image; and
- generating an image recognition result corresponding to the medical image according to the thermodynamic diagram and the object contour map.

18. The non-transitory computer-readable storage medium according to claim 17, wherein obtaining the feature map and the medical image content recognition result comprises:
- obtaining the feature map corresponding to the medical image by using a convolutional layer of the medical image classification model;
- processing the feature map by using a global average pooling (GAP) layer of the medical image classification model, to obtain a feature vector;
- calculating C class prediction scores according to the feature vector and the weight parameter set, each class prediction score being corresponding to one class, C being an integer greater than or equal to 1; and
- determining the medical image content recognition result from C classes according to the C class prediction scores.

19. The non-transitory computer-readable storage medium according to claim 17, wherein obtaining the gradient propagation result according to the medical image content recognition result or the lesion classification result comprises:
- obtaining the gradient propagation result according to the medical image content recognition result or the lesion classification result based on a guided backpropagation algorithm, the guided backpropagation algorithm being used for back passing a feature corresponding to a position in which both a gradient and an input value are greater than 0.

* * * * *